(12) United States Patent
Schumacher et al.

(10) Patent No.: US 11,780,884 B2
(45) Date of Patent: Oct. 10, 2023

(54) RUBELLA VIRUS SPIKE CONSTRUCT

(71) Applicants: Institut Virion \ Serion GmbH, Wuerzburg (DE); Judith Stuermer, Wuerzburg (DE)

(72) Inventors: Thomas Schumacher, Erlangen (DE); Hugo Arends, Wuerzburg (DE)

(73) Assignees: Judith Stuermer, Wuerzburg (DE); Institut Virion \ Serion GmbH, Wuerzburg (DE)

( * ) Notice: Subject to any disclaimer, the term of this patent is extended or adjusted under 35 U.S.C. 154(b) by 282 days.

(21) Appl. No.: 15/734,263

(22) PCT Filed: Feb. 14, 2020

(86) PCT No.: PCT/DE2020/000024
§ 371 (c)(1),
(2) Date: Dec. 2, 2020

(87) PCT Pub. No.: WO2021/004561
PCT Pub. Date: Jan. 14, 2021

(65) Prior Publication Data
US 2021/0261624 A1    Aug. 26, 2021

(30) Foreign Application Priority Data
Jul. 10, 2019  (DE) .................... 10 2019 004 812.1

(51) Int. Cl.
*C12N 7/00* (2006.01)
*C07K 14/005* (2006.01)
(Continued)

(52) U.S. Cl.
CPC ............ *C07K 14/005* (2013.01); *A61K 39/20* (2013.01); *G01N 33/56983* (2013.01);
(Continued)

(58) Field of Classification Search
None
See application file for complete search history.

(56) References Cited

U.S. PATENT DOCUMENTS
6,670,117 B2    12/2003    Dorsett et al.

FOREIGN PATENT DOCUMENTS
| EP | 1780282 A1 | 5/2007 |
| EP | 2222694 B1 | 1/2014 |
| EP | 2307543 B1 | 5/2015 |

OTHER PUBLICATIONS

Battisti et al., 2012. Cryo-Electron Tomography of Rubella Virus, J Virol. Oct. 2012; 86(20): 11078-11085, total of 8 pages.
(Continued)

*Primary Examiner* — M Franco G Salvoza
(74) *Attorney, Agent, or Firm* — Collard & Roe, P.C.

(57) ABSTRACT

The Rubella Virus Spike construct comprises at least one E1 component and one E2 component, which are linked together. The E1 component consists of the E1 envelope protein, whose C-terminal transmembrane region and intravirional domain are removed and whose N-terminus comprises the ectodomain of the E1 envelope protein. The E2 component consists of the E2 envelope protein whose transmembrane regions and intravirional domain removed and whose C-terminus comprising the ectodomain of the E2 envelope protein.
The C-terminus of the E2 component is connected to the N-terminus of the E1 component by direct fusion or by means of a linker to form an E1-E2 fusion protein.

20 Claims, 14 Drawing Sheets

Figure 1:
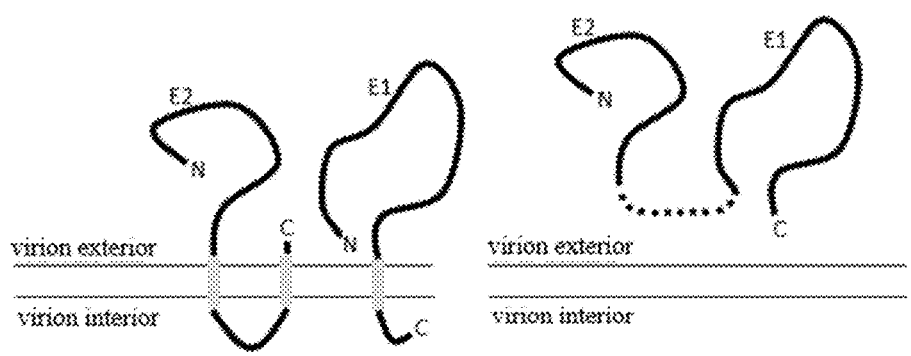

Specification includes a Sequence Listing.

(51) Int. Cl.
    *A61K 39/20* (2006.01)
    *G01N 33/569* (2006.01)
(52) U.S. Cl.
    CPC .............. *C12N 2770/36222* (2013.01); *C12N 2770/36234* (2013.01); *C12N 2770/36251* (2013.01); *G01N 2333/19* (2013.01); *G01N 2469/20* (2013.01)

(56) References Cited

OTHER PUBLICATIONS

DuBois et al., 2013. Functional and evolutionary insight from the crystal structure of rubella virus protein E1. Nature. Jan. 24, 2013;493(7433):552-556, total of 6 pages.

Hobman et al., 1993: The Rubella Virus E2 and E1 Spike Glycoproteins are Targeted to the Golgi Complex. J. Cell Biol. 121: 269-281 (1993), total of 13 pages.

Hobman et al., 2007. Fields Virology vol. 1 (ed. D. M Knipe) Chapter 32, 1069-1100 (Lippincott Williams & Wilkins, 2007), total of 72 pages.

Katow et al., 1988. Low pH-induced Conformational Change of Rubella Virus Envelope Proteins. J Gen Virol 1988;69(pt 11):2797-2807, total of 11 pages.

Perrenoud G. et al. 2004: A recombinant rubella virus E1 glycoprotein as a rubella vaccine candidate. Vaccine 2004;23(4):480-488, total of 9 pages.

Prasad et al., 2017. Assembly, maturation and three-dimensional helical structure of the teratogenic rubella virus. PLoS Pathog. Jun. 2, 2017;13(6), total of 18 pages.

Schneider, I., 1972. Cell lines derived from late embryonic stages of *Drosophila melanogaster*. Journal of Embryology and Experimental Morphology 27 (2): 353-365. http://www.ncbi.nlm.nih.gov/pubmed/4625067, total of 13 pages.

Seppänen et al. 1991: Diagnostic Potential of Baculovirus-Expressed Rubella Virus Envelope Proteins. Clin. Microbiol, 1991, 1877-1882, total of 6 pages.

Waxham et al., 1985. Detailed Immunologic Analysis of the Structural Polypeptides of Rubella Virus Using Monoclonal Antibodies. Virology 1985;143:153-165, total of 13 pages.

Elgenaid, S. et al., "Prediction of Multiple Peptide Based Vaccine from E1, E2 and Capsid Proteins of Rubella Virus: An In-Silico Approach", Immunome Research, 14:1, 2018, pp. 1-13.

Dubé et al. 2014, "Rubella Virus: First Calcium-Requiring Viral Fusion Protein", PLOS Pathogens, Dec. 2014, vol. 10, Issue 12, e1004530, total of 13 pages.

Nedeljkovic et al. 1999, "Immunoblot analysis of natural and vaccine-induced IgG responses to rubella virus proteins expressed in insect cells", Journal of Clinical Virology 14 (1999), pp. 119-131, total of 13 pages.

Orellana et al. 1999, "Mimicking rubella virus particles by using recombinant envelope glycoproteins and liposomes", Journal of Biotechnology 75 (1999), pp. 209-219, total of 11 pages.

Petrova, E.K., et al. The key role of rubella virus glycoproteins in the formation of immune response, and perspectives on their use in the development of new recombinant vaccines. Vaccine (2016), total of 6 pages. http://dx.doi.org/10.1016/j.vaccine.2016.01.010.

Qiu et al 1994, "Expression and Characterization of Virus-Like Particles Containing Rubella Virus Structural Proteins", Journal of Virology, Jun. 1994, vol. 68, No. 6, p. 4086-4091, total of 6 pages.

Lampinen, Vili, Master's thesis, University of Tampere, Faculty of Medicine and Life Sciences, Apr. 2018, "Development of antigen-decorated norovirus-like particles for vaccine applications", total of 65 pages, https://core.ac.uk/download/pdf/250169644.pdf.

Entry on UniProtKB | UniProt, "Gene:gB, Protein: Envelope glycoprotein B, Organism: Epstein-Barr virus (strain AG876) (HHV-4)", Last updated Sep. 22, 2009, total of 5 pages, https://www.uniprot.org/uniprotkb/P0C763/entry.

Zhang et al., "Structure of SARS-CoV-2 membrane protein essential for virus assembly", Nature Communications, 2022, 13:4399, pp. 1-12, https://www.nature.com/articles/s41467-022-32019-3.

Entry on UniProtKB | UniProt, "Protein: Structural polyprotein, Organism: Rubella virus (strain M33) (RUBV)", Last updated May 30, 2006, total of 8 pages, https://www.uniprot.org/uniprotkb/P08563/entry.

MKLCILLAVVAFVGLSLGGLQPRADMAAPPMPPQPPRAHGQHYGHHHHQLPFLGHDGHHGGTLRVGQH
HRNASDVLPGHWLQGGWGCYNLSDWHQGTHVCHTKHMDFWCVEHDRPPPATPTSLTTAANSTTAATPA
TAPPPCHAGLNDSCGGFLSGCGPMRLRHGADTRCGRLICGLSTTAQYPPTRFGCAMRWGLPPWELVVL
TARPEDGWTCRGVPAHPGTRCPELVSPMGRATCSPASALWLATANALSggsggsggsgggsgggsgsg
ggggEEAFTYLCTAPGCATQTPVPVRLAGVRFESKIVDGGCFAPWDLEATGACICEIPTDVSCEGLGA
WVPTAPCARIWNGTQRACTFWAVNAYSSGGYAQLASYFNPGGSYYKQYHPTACEVEPAFGHSDAACWG
FPTDTVMSVFALASYVQHPHKTVRVKFHTETRTVWQLSVAGVSCNVTTEHPFCNTPHGQLEVQVPPDP
GDLVEYIMNYTGNQQSRWGLGSPNCHGPDWASPVCQRHSPDCSRLVGATPERPRLRLVDADDPLLRTA
PGPGEVWVTPVIGSQARKCGLHIRAGPYGHATVEMPEWIHAHTTSDPWHPPGPLGLKFKTVRPVALPR
ALAPPRNVRVTGCYQCGTPALVEGLAPGGGNCHLTVNGEDVGAFPPGKFVTAALLNTPPPYQVSCGGE
SDRASARVIDPAAQSFTGVVYGTHTTAVSETRQTWAEWAAAH

SEQ ID NO:2

(A)

MKLCILLAVVAFVGLSLGGLQPRADMAAPPMPPQPPRAHGQHYGHHHHQLPFLGHDGHHGGTLRVGQH
HRNASDVLPGHWLQGGWGCYNLSDWHQGTHVCHTKHMDFWCVEHDRPPPATPTSLTTAANSTTAATPA
TAPPPCHAGLNDSCGGFLSGCGPMRLRHGADTRCGRLICGLSTTAQYPPTRFGCAMRWGLPPWELVVL
TARPEDGWTCRGVPAHPGTRCPELVSPMGRATCSPASALWLATANALSggsggsggEEAFTYLCTAPG
CATQTPVPVRLAGVRFESKIVDGGCFAPWDLEATGACICEIPTDVSCEGLGAWVPTAPCARIWNGTQR
ACTFWAVNAYSSGGYAQLASYFNPGGSYYKQYHPTACEVEPAFGHSDAACWGFPTDTVMSVFALASYV
QHPHKTVRVKFHTETRTVWQLSVAGVSCNVTTEHPFCNTPHGQLEVQVPPDPGDLVEYIMNYTGNQQS
RWGLGSPNCHGPDWASPVCQRHSPDCSRLVGATPERPRLRLVDADDPLLRTAPGPGEVWVTPVIGSQA
RKCGLHIRAGPYGHATVEMPEWIHAHTTSDPWHPPGPLGLKFKTVRPVALPRALAPPRNVRVTGCYQC
GTPALVEGLAPGGGNCHLTVNGEDVGAFPPGKFVTAALLNTPPPYQVSCGGESDRASARVIDPAAQSF
TGVVYGTHTTAVSETRQTWAEWAAAH

SEQ ID NO:4

(B)

Fig. 2

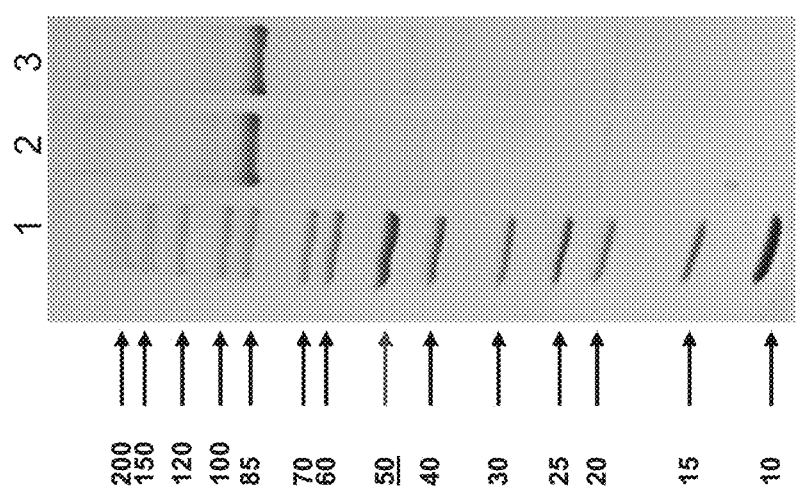

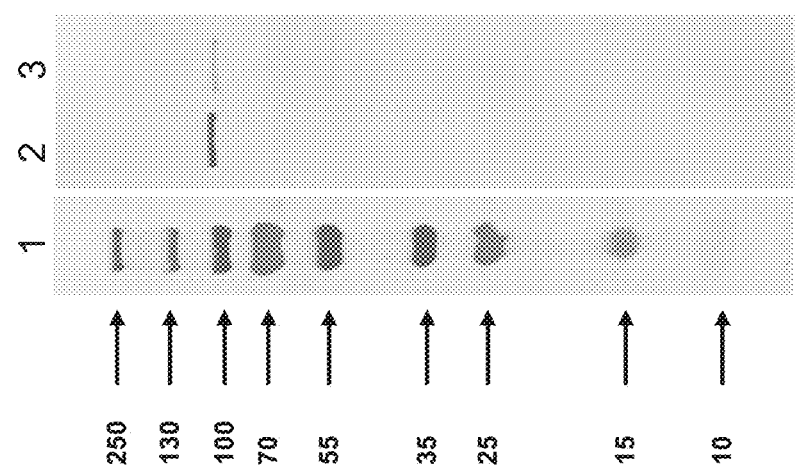

Detection of anti-Rubella IgM antibodies in human sera using Rubella spike constructs compared to the whole virus as antigen

| | ID | Reference ELISA | | "Spike-long" ELISA | | "Spike-short" ELISA | | "Spike-long" Particle | | "Spike-short" Particle | |
|---|---|---|---|---|---|---|---|---|---|---|---|
| | | OD | Evaluation | OD | Evaluation | OD | Evaluation | MFI | Evaluation | MFI | Evaluation |
| Panel 1 | 5 | 0,521 | pos | 0,165 | eq | 0,089 | *neg* | 6708 | *neg* | 4842 | *neg* |
| | 6 | 0,361 | eq | 0,323 | pos | 0,176 | pos | 11118 | pos | 9571 | pos |
| | 32 | 0,324 | eq | 0,166 | eq | 0,115 | eq | 3931 | *neg* | 3695 | *neg* |
| | 35 | 1,374 | pos | 1,388 | pos | 1,209 | pos | 8096 | pos | 8485 | pos |
| | 44 | 1,121 | pos | 0,633 | pos | 0,456 | pos | 13456 | pos | 18698 | pos |
| | 45 | 0,911 | pos | 0,446 | pos | 0,330 | pos | 8119 | pos | 7093 | pos |
| | 49 | 1,065 | pos | 0,545 | pos | 0,416 | pos | 10796 | pos | 8485 | pos |
| | 50 | 1,081 | pos | 0,499 | pos | 0,343 | pos | 11550 | pos | 10828 | pos |
| | 52 | 0,968 | pos | 0,423 | pos | 0,299 | pos | 10120 | pos | 9349 | pos |
| | 53 | 1,034 | pos | 0,419 | pos | 0,331 | pos | 10453 | pos | 9459 | pos |
| | 81 | 0,595 | pos | 0,279 | pos | 0,196 | pos | 11052 | pos | 10300 | pos |
| | 167 | 1,680 | pos | 0,801 | pos | 0,605 | pos | 9656 | pos | 10453 | pos |
| | 170 | 1,117 | pos | 0,275 | pos | 0,141 | pos | 8411 | pos | 8361 | pos |
| | 175 | 1,023 | pos | 0,526 | pos | 0,375 | pos | 11483 | pos | 10955 | pos |
| | 176 | 0,874 | pos | 0,472 | pos | 0,312 | pos | 12000 | pos | 9078 | pos |
| | 177 | 3,135 | pos | 3,107 | pos | 2,558 | pos | 105771 | pos | 103315 | pos |
| | 179 | 2,469 | pos | 1,802 | pos | 1,256 | pos | 39774 | pos | 33643 | pos |
| | 203 | 1,000 | pos | 0,849 | pos | 0,649 | pos | 10150 | pos | 9321 | pos |
| | 204 | 0,842 | pos | 0,393 | pos | 0,264 | pos | 10859 | pos | 10514 | pos |

Fig. 8A

|  |  |  |  |  |  |  |  |
|---|---|---|---|---|---|---|---|
| Panel 2 | 5 | 0,071 | neg | 0,065 | neg | 1994 | neg | 1994 | neg |
|  | 6 | 0,066 | neg | 0,034 | neg | 1763 | neg | 1805 | neg |
|  | 10 | 0,147 | neg | 0,038 | neg | 3394 | neg | 3374 | neg |
|  | 11 | 0,163 | neg | 0,085 | neg | 3144 | neg | 3200 | neg |
|  | 13 | 0,050 | neg | 0,015 | neg | 1727 | neg | 1848 | neg |
|  | 15 | 0,077 | neg | 0,029 | neg | 1789 | neg | 1886 | neg |
|  | 17 | 0,043 | neg | 0,014 | neg | 1925 | neg | 1931 | neg |
|  | 30 | 0,087 | neg | 0,050 | neg | 2066 | neg | 2121 | neg |
| Panel 3 | 5 | 0,129 | neg | 0,034 | neg | 3181 | neg | 2747 | neg |
|  | 7 | 0,210 | neg | 0,022 | neg | 2344 | neg | 2090 | neg |
|  | 8 | 0,174 | neg | 0,014 | neg | 3589 | neg | 3631 | neg |
|  | 10 | 0,046 | neg | 0,035 | neg | 4688 | neg | 5478 | neg |
|  | 12 | 0,140 | neg | 0,035 | neg | 2552 | neg | 2250 | neg |
|  | 13 | 0,142 | neg | 0,051 | neg | 2250 | neg | 2210 | neg |
|  | 14 | 0,066 | neg | 0,014 | neg | 1692 | neg | 1687 | neg |
|  | 15 | 0,053 | neg | 0,010 | neg | 1662 | neg | 1518 | neg |
|  | 16 | 0,045 | neg | 0,003 | neg | 1591 | neg | 1545 | neg |
|  | 17 | 0,030 | neg | 0,016 | neg | 1937 | neg | 1892 | neg |
|  | 18 | 0,075 | neg | 0,042 | neg | 3305 | neg | 3296 | neg |

Fig. 8B

Detection of anti-Rubella IgG antibodies in human sera using Rubella spike constructs compared to the whole virus as antigen

| | ID | Reference ELISA | | "Spike-long" ELISA | | "Spike-short" ELISA | | "Spike-long" Particle | | "Spike-short" Particle | |
|---|---|---|---|---|---|---|---|---|---|---|---|
| | | OD | Evaluation | OD | Evaluation | OD | Evaluation | MFI | Evaluation | MFI | Evaluation |
| Panel 1 | 87 | 1,258 | pos | 1,817 | pos | 1,769 | pos | 402000 | pos | 424000 | pos |
| | 89 | 1,311 | pos | 1,927 | pos | 1,699 | pos | 355776 | pos | 382883 | pos |
| | 91 | 1,005 | pos | 1,621 | pos | 1,559 | pos | 371801 | pos | 376195 | pos |
| | 92 | 1,118 | pos | 1,659 | pos | 1,507 | pos | 280450 | pos | 306283 | pos |
| | 94 | 0,666 | pos | 1,148 | pos | 1,116 | pos | 165779 | pos | 166267 | pos |
| | 96 | 1,064 | pos | 1,733 | pos | 1,633 | pos | 358925 | pos | 365306 | pos |
| Panel 2 | XF11 | 0,732 | pos | 0,994 | pos | 0,793 | pos | 131450 | pos | 124315 | pos |
| | XF16 | 0,931 | pos | 1,412 | pos | 1,265 | pos | 161454 | pos | 172738 | pos |
| | XF35 | 0,787 | pos | 1,162 | pos | 0,949 | pos | 106082 | pos | 109566 | pos |
| | XF36 | 1,379 | pos | 2,067 | pos | 1,848 | pos | 486000 | pos | 520000 | pos |
| | XF38 | 0,801 | pos | 1,333 | pos | 1,058 | pos | 69293 | pos | 65532 | pos |
| | XF39 | 1,288 | pos | 1,955 | pos | 1,892 | pos | 564000 | pos | 584000 | pos |
| | XF41 | 1,497 | pos | 2,004 | pos | 1,912 | pos | 581000 | pos | 629000 | pos |
| | XF45 | 1,114 | pos | 1,617 | pos | 1,503 | pos | 318204 | pos | 332536 | pos |
| Panel 3 | 16 | 1,148 | pos | 1,543 | pos | 1,359 | pos | 245008 | pos | 240728 | pos |
| | 22 | 1,094 | pos | 1,567 | pos | 1,5 | pos | 267576 | pos | 280450 | pos |
| | 23 | 1,155 | pos | 1,617 | pos | 1,569 | pos | 329619 | pos | 341444 | pos |
| | 24 | 1,146 | pos | 1,639 | pos | 1,582 | pos | 322911 | pos | 322911 | pos |
| | 26 | 1,057 | pos | 1,522 | pos | 1,421 | pos | 249364 | pos | 258309 | pos |
| | 27 | 0,898 | pos | 1,127 | pos | 0,966 | pos | 95438 | pos | 104843 | pos |
| | 28 | 1,112 | pos | 1,586 | pos | 1,437 | pos | 232391 | pos | 242146 | pos |

Fig. 9A

| Panel 4 | | | | | | | |
|---|---|---|---|---|---|---|---|
| 133 | 0,057 | neg | 0,11 | neg | 0,105 | neg | 3374 | neg | 2922 | neg |
| 137 | 0,057 | neg | 0,072 | neg | 0,075 | neg | 4460 | neg | 3325 | neg |
| 156 | 0,040 | neg | 0,041 | neg | 0,038 | neg | 2344 | neg | 2000 | neg |
| 157 | 0,024 | neg | 0,032 | neg | 0,032 | neg | 2134 | neg | 1994 | neg |
| 158 | 0,409 | eq | 0,582 | eq | 0,447 | eq | 68082 | pos | 69906 | pos |
| 159 | 0,350 | neg | 0,652 | eq | 0,55 | eq | 71358 | pos | 70111 | pos |
| 166 | 0,025 | neg | 0,041 | neg | 0,042 | neg | 3257 | neg | 3172 | neg |
| 204 | 0,294 | neg | 0,641 | eq | 0,626 | eq | 91057 | pos | 91594 | pos |
| 206 | 0,135 | neg | 0,275 | neg | 0,24 | neg | 27796 | neg | 28709 | neg |
| 208 | 0,056 | neg | 0,119 | neg | 0,102 | neg | 9571 | neg | 8893 | neg |
| 210 | 0,055 | neg | 0,111 | neg | 0,106 | neg | 10180 | neg | 9571 | neg |
| 211 | 0,052 | neg | 0,106 | neg | 0,089 | neg | 9212 | neg | 8764 | neg |
| 212 | 0,161 | neg | 0,307 | neg | 0,276 | neg | 30535 | neg | 30535 | neg |
| 214 | 0,214 | neg | 0,363 | neg | 0,326 | neg | 48567 | neg | 46474 | neg |
| 215 | 0,315 | neg | 0,563 | eq | 0,458 | eq | 57418 | eq | 56915 | neg |
| 217 | 0,032 | neg | 0,039 | neg | 0,038 | neg | 2613 | neg | 2296 | neg |
| 218 | 0,038 | neg | 0,045 | neg | 0,042 | neg | 2583 | neg | 2323 | neg |
| 219 | 0,033 | neg | 0,047 | neg | 0,042 | neg | 2731 | neg | 2414 | neg |
| 220 | 0,203 | neg | 0,344 | neg | 0,315 | neg | 35159 | neg | 34850 | neg |
| 221 | 0,066 | neg | 0,046 | neg | 0,051 | neg | 2435 | neg | 2243 | neg |
| 223 | 0,198 | neg | 0,335 | neg | 0,295 | neg | 28125 | neg | 28374 | neg |
| 224 | 0,202 | neg | 0,361 | neg | 0,345 | neg | 31170 | neg | 32099 | neg |
| 225 | 0,234 | neg | 0,408 | neg | 0,377 | neg | 39658 | neg | 40009 | neg |
| 226 | 0,219 | neg | 0,376 | neg | 0,324 | neg | 39891 | neg | 40009 | neg |

Fig. 9B

RUBELLA VIRUS SPIKE CONSTRUCT

CROSS REFERENCE TO RELATED APPLICATIONS

This application is the National Stage of PCT/DE2020/000024 filed on Feb. 14, 2020, which claims priority under 35 U.S.C. § 119 of German Application No. 10 2019 004 812.1 filed on Jul. 10, 2019, the disclosure of which is incorporated by reference. The international application under PCT article 21(2) was not published in English.

SEQUENCE LISTING STATEMENT

Applicant hereby incorporates by reference the material in the ASCHII text file Rubella Spikes 20190704_Sequence Listing-Rectification_ST25 (Textdokument). Created on Dec. 1, 2020 and having a file size of 27 kilobytes.

The invention relates to a rubella virus spike construct suitable and intended for diagnostic and/or therapeutic applications.

The rubella virus (in German: Roteln-Virus) is the causative agent of rubella (rubeola). Rubella is an aerogenic (i.e. spreading through the air) highly contagious infectious disease that leaves a lifelong immunity. In children, the typical symptoms of rubella are red skin spots (exanthema), fever and possibly swelling of the lymph nodes. Complications are usually rare. However, rubella infection during pregnancy can lead to serious complications with pronounced malformations of the child and miscarriages. If a pregnant woman becomes infected with rubella virus (RUBY) during the first three months of pregnancy, there is a 20% risk that the fetus will develop congenital rubella syndrome (CRS). RUBY is endemic worldwide and infection can be prevented by vaccination (Hobman et al., 2007).

The Rubella virus is the only member of the genus Rubivirus and belongs to the family Togaviridae, whose genome typically consists of a single-stranded RNA with positive polarity. The RNA genome is surrounded by an icosahedral capsid (T=4 symmetry) and has a length of about 10 kb (10,000 nucleotides). It encodes three structural proteins, namely the capsid protein (31 kDa) and the two envelope proteins E1 (58 kDa) and E2 (42-47 kDa), and two non-structural proteins (p150 and p90) (Hobman et al., 2007). The capsid is surrounded by a lipid membrane (virus envelope) derived from the host cell membrane. The two envelope proteins E1 and E2 are embedded in this lipid membrane in the form of heterodimers. Both envelope proteins (E1 and E2) are glycoproteins and anchored in the viral membrane by C-terminal transmembrane domains (DuBois et al., 2012).

The rubella virions (synonym for: rubella virus particles outside a host cell) have a size of 50 to 70 nm in diameter. The virions form a variety of shapes ranging from nearly spherical to elongated tubular structures (Battisti et al., 2012). According to current knowledge, the shape of the surface structure is the same for all Rubella virions, and therefore only one serotype exists.

The envelope protein E1 is responsible for the recognition and binding of rubella virions to cellular receptors (of the host cells) and it is involved in membrane fusion (DuBois et al., 2012). The envelope protein E2 is required for the efficient folding and transport of E1 through the relevant compartments of the host cell. Of the two envelope proteins, only the structure of the E1 ectodomain in its trimeric, post-fusion conformation is known (Prasad et al., 2017).

Both envelope proteins E1 and E2 are transmembrane glycoproteins of type I. On the surface of the virion (virion=virus particles outside the host cell) they are present as a heterodimeric rubella virus E1 and E2 glycoprotein complex in the form of the so-called spikes (synonyms: rubella spikes; E1-E2 protein complex; E1-E2 heterodimer).

During the biogenesis of the rubella virus in the host cell, first, in the course of translation, a structural polyprotein is synthesized, which is cleaved by signal peptidases into the capsid protein and the two envelope proteins E1 and E2. The dimerization of E1 and E2 takes place in the endoplasmic reticulum. As a chaperone, E2 promotes the folding and thus the structural integrity of E1. In contrast to other togavidirae, E1 and E2 of rubella virus do not undergo a proteolytic maturation step. Rubella virus particles are produced in the Golgi apparatus, they undergo the usual secretion pathway and are finally released into the extracellular milieu. (Dube et al. 2014.)

The main functions of these spikes (synonym: rubella spikes) are the binding to/with receptors of the host cell and the mediation of the fusion with (host) cell membranes (Katow et al., 1988).

In the state of the art it has long been accepted that the envelope protein E1 is the major antigenic determinant against which neutralizing antibodies of the host organism are directed (Waxham et al., 1985). But also the envelope protein E2 and the capsid protein C are among the targets of the humoral immune response to rubella infection. In sera of individuals (patients) infected with rubella, antibodies against E1 and E2 are regularly abundant.

A comparison (by Nedelkovic et al. 1999) of the diagnostic potentials of (in Sf9 insect cells with the baculovirus system) recombinantly produced rubella proteins C, E1 and E2 in immunoblot and enzyme immunoassay (EIA) showed that the recombinant proteins E1 and C predominantly triggered the immune response, both in postnatal and in vaccinal rubella virus infections. The immune response against the recombinant E2 protein was significantly weaker, but in the case of a congenital infection it was significantly stronger.

Several approaches to produce the Rubella El envelope protein for diagnostic purposes are known in the state of the art. Many efforts have been made to produce stable and soluble fragments of E1 with high antigenicity and in large quantities. One method for this was the production of stably infected/transfected cell lines that recombinantly express E1 and/or E2. For example, Seppanen et al. (1991) already described the expression of rubella glycoproteins E1 and E2 in *Spodoptera frugiperda* Sf9 insect cells using the baculovirus expression system.

EP1780282A1 describes the recombinant expression and production of a soluble modified Rubella E1 envelope protein lacking at least the C-terminal transmembrane region, the anchor segment and amino acid 143 to 164 in the middle part of the protein molecule. This modified E1 envelope protein contains at least that region of the rubella E1 amino acid sequence that spans the disulfide bridges Cys 349-Cys 352 and Cys 368-Cys 401 and comprises at least amino acids 315-412, and it is fused with an FKBP chaperone. According to the teaching of EP1780282A1, it is essential that both disulfide bridges in the C-terminal part are intact, i.e. closed, in order to obtain a Rubella El variant that is sufficiently antigenic and suitable for antibody detection.

EP 2222694A1 reveals the production of further recombinantly expressed soluble rubella E1 envelope antigens, which, compared to the native E1 envelope protein, lack the transmembrane region and the C-terminal anchor segment as well as the segment with amino acids 143 to 164 in the middle part of the molecule, and which contain at least two disulfide bonds, one formed between Cys 225 and Cys 235 (C13-C14) and the other formed between Cys 349 and Cys 352 (C17-C18).

Oreliana et al. 1999 describe the generation of so-called "rubella virus mimicking proteoliposomes", i.e. liposomes that carry (in Sf9 insect cells with the baculovirus system) recombinantly produced rubella virus envelope proteins E1 and E2 exposed. These rubella virus mimicking proteoliposomes were recognized by antibodies with specificity for the rubella virus proteins E1 and E2.

The known recombinantly produced and not further assembled rubella antigens, namely glycoprotein E1, glycoprotein E2 and capsid protein have the disadvantage that their reactivity in immunoassays and/or their production is limited. In the acute phase of a rubella virus infection, the patient organism mainly produces IgM antibodies against glycoprotein E1 and E2, which are presented to the immune system in the form of heterodimers or rather spikes. However, if glycoprotein E1 or E2 are produced separately using recombinant protein expression systems according to the state of the art, no heterodimers are produced. Even a subsequent assembly of purified glycoprotein E1 and E2 does not lead to a natural assembly of heterodimeric spikes.

So-called "virus-like particles" (VLPs) have also been known for a long time in the state of the art, also from rubella virus (RLPs—Rubella-Like Particles). Various studies have shown that the expression of the three rubella structural proteins C, E1, and E2 in stably transfected CHO or BHK cell lines leads to the production of rubella-like VLPs, whose size, morphology and density were identical to those of the native rubella virus, but which were non-infectious. These rubella VLPs were used to detect human anti-rubella virus antibodies in diagnostic immunoassays. Furthermore, immunization in mice was achieved with these Rubella VLPs, namely the generation of specific antibodies against rubella virus structural proteins and of virus neutralizing and hemagglutination-inhibiting antibodies (see review by Petrova et al. 2016). For the recombinant production of Rubella VLPs, all structural proteins, glycoprotein E1, glycoprotein E2 and the capsid protein, are generally expressed. The VLPs that are formed consist of the capsid surrounded by a lipid bilayer in which the viral glycoproteins E1 and E2 are embedded. The VLPs are thus structurally very similar to the native Rubella viruses. A disadvantage of the application of Rubella VLPs in immunoassays is the presence of the capsid protein, which is suspected to cause cross reactions (see U.S. Pat. No. 6,670,117B2). Especially IgM immunoassays are very susceptible to cross reactivity. Furthermore, the production of rubella VLPs is associated with several disadvantages: The expression rate in the required eukaryotic expression systems is usually extremely low. The VLPs must be purified from cell lysates or from cell culture supernatants, which often results in considerable yield losses. The VLP preparations contain more impurities than recombinant antigens (purified by an affinity tag), which increases the risk of unspecific reactions.

Rubella virus state of the art vaccines are mainly based on attenuated rubella virus strains. However, these strains have serious disadvantages: they cannot be used in pregnant women or people with immunodeficiency. Side effects such as arthritis, diabetes, damage to the central nervous system as well as allergic and anaphylactic reactions often occur. Production, transport and storage are costly. (Hobman et al 1994, Qiu et al 1994 —Review by Petrova et al 2016).

A promising replacement for the live vaccine is currently seen in a recombinant rubella envelope protein E1. (Perrenoud G. et al. 2004 —Review by Petrova et al. 2016).

There is still a demand for rubella antigen preparations that present as many different epitopes of the native infectious rubella virus as possible and are therefore suitable for binding and thus detecting various anti-rubella antibodies from human patient samples in diagnostic systems, e.g. ELISA or CLIA systems, and/or as vaccine agent for triggering the formation of antibodies in the patient's organism.

The present invention is based on the problem of providing new rubella antigens which are highly soluble and immunologically highly reactive (i.e. highly antigenic), and which are well suited for the reliable detection of rubella infection, i.e. an infection with the pathogen rubella, and/or as an active substance of a vaccine.

One solution of this problem is the specification of a rubella virus E1-E2 envelope protein complex construct, or "rubella spike construct" for short, which is characterized, in that it comprises at least one E1 component and one E2 component, which are connected (or coupled) to one another (either immediately or directly, or indirectly), in that the E1 component consists of the E1 envelope protein whose C-terminal transmembrane region and intravirional domain are removed and whose N-terminus comprises the ectodomain of the E1 envelope protein, in that the E2 component consists of the E2 envelope protein whose transmembrane regions and intravirional domain are removed and whose N-terminus comprises the ectodomain of the E2 envelope protein, and in that the C-terminus of the E2 component (i.e. the C-terminus of the ectodomain of the E2 envelope protein) is connected (coupled) directly (in direct fusion) or indirectly, namely by means of or via a linker, to the N-terminus of the E1 component (i.e. to the N-terminus of the ectodomain of the E1 envelope protein), so that an E1-E2 fusion protein is present.

Surprisingly, it was found that such inventive rubella spike constructs, i.e. E1-E2 fusion proteins, after expression in the host cell are successfully processed in the ER (endoplasmic reticulum) and Golgi apparatus and secreted in soluble form, and that they are obviously immunologically similar to a native heterodimer in such a way, that they are recognized and bound like this by human anti-rubella virus antibodies (e.g. from patient sera) in known diagnostic test systems.

Preferably, the E1-E2 fusion protein of the rubella spike construct according to the invention is additionally fused (coupled) with a signal sequence (synonyms: signal peptides, transit peptides).

Signal sequences are relatively short (about 20-30 amino acids) amino acid sequences located at the N-terminus of proteins and contain information for the secretion of this protein, especially for its transport path and possibly also its folding. They occur ubiquitously in prokaryotes and eukaryotes and basically consist of three sections: a positively charged amino-terminal section (N region), a middle hydrophobic section (H region) and a slightly polar carboxy section (C region). From numerous different studies on the production of recombinant proteins in cell lines it is known that the secretion efficiency and thus the production rate of the recombinant protein can be significantly increased by the use of signal sequences.

Preferably, the E1-E2 fusion protein according to the invention is provided (coupled) with an affinity tag to allow effective purification, especially in the case of recombinant production. Especially a streptavidin affinity tag (Streptag, Twin Streptag) or a polyhistidine tag (His tag) can be used as affinity tag. According to the invention, the affinity tag is preferably coupled to the C-terminal, an arrangement (positioning) at the N-terminus or in the linker is also possible.

Preferably, the ectodomain of the E1 envelope protein comprises the amino acids (of positions) 1-446 according to SEQ ID NO:6 or (correspondingly) the amino acids AA583-1028 in the reference sequence UniProtKB/SwissProt—P08563 (POLS_RUBVM), Sequence Update May 30, 2006 (version 2 of the sequence).

Preferably, the ectodomain of the E2 envelope protein comprises the amino acids (of positions) 1-234 according to SEQ ID NO:8 or (correspondingly) the amino acids AA301-534 in the reference sequence UniProtKB/SwissProt—P08563 (POLS_RUBVM), Sequence Update May 30, 2006 (version 2 of the sequence).

If a linker is used, it is preferably a flexible linker, which further preferably consists entirely or predominantly of glycine and serine, and which can be designed in particular as a short linker or long linker.

The size or length of the linker may have an influence on the antigenic properties of the rubella spikes. In practice, it has been observed that,—depending on the diagnostic platform used and especially when glycine serine linkers are used,—spike constructs with a 24 aa linker often show better antigenic properties than spike constructs with an 8 aa linker.

By modifying the linker, in particular by selecting its size or length and/or amino acid composition, the rubella antigen can be optimized and tailored for specific diagnostic or therapeutic applications ("tailor-made-antigens").

The generation (manufacturing/production) of the rubella spike construct according to the invention is preferably carried out in eukaryotic cell cultures using expression vectors.

For this purpose, a recombinant nucleotide sequence coding for the rubella E1-E2 fusion protein according to the invention is generated with those RNA sequences coding for the envelope protein components and, if necessary, with the nucleotide sequence coding for the selected linker sequence, and this recombinant nucleotide sequence is inserted into an expression vector in operative linkage.

The invention therefore also relates to such recombinant nucleotide sequences (synonym: recombinant DNA molecules) and preferably those comprising the nucleotide sequences according to SEQ ID NO:5 and SEQ ID NO:7.

Particularly preferred recombinant nucleotide sequences or DNA molecules which have already proved to be effective in practice are characterized in that they comprise the nucleotide sequence according to SEQ ID NO: 1 and/or the nucleotide sequence according to SEQ ID NO: 3, whereby the signal sequence is optionally present at the N-terminal end, i.e. it may be missing or replaced by a similarly functioning and effective one.

Preferred E1-E2 fusion proteins or rubella spike constructs are characterized in that they comprise the amino acid sequence according to SEQ ID NO: 2 or according to SEQ ID NO: 4, wherein the signal sequence at the N-terminal end and/or the linker sequence in the middle region of these amino acid sequences is optionally present, i.e. it may be missing or replaced by a similarly functioning and acting one.

The invention therefore also relates to an expression vector which, when operatively linked, comprises a nucleotide sequence which codes for the rubella E1 and E2 envelope protein components in the spike construct, i.e. (in simplified form) for the rubella E1-E2 fusion protein.

The expression vector is preferably a transfer vector according to EP2307543B1; for example, the transfer vector "pExpres2.1", commercially available from Expres2ion Biotechnologies, Horsholm, Denmark.

The invention also relates to a host cell transformed with an expression vector comprising, in operative linkage, a nucleotide sequence which codes for the rubella E1 and E2 envelope protein components in the spike construct, i.e. (in simplified form) for the rubella E1-E2 fusion protein.

A *Drosophila* Schneider 2 (S2) cell (cf. Schneider 1972) is preferably used as host cell.

The *Drosophila* S2 cell line is commercially available, deposited at DSMZ (Braunschweig, Germany) under depot number DSMZ ACC 130 and at ATCC (American Type Culture Collection, P.O. Box 1549, Manassas, Va., USA) under depot number CRL-1963 and is accessible to the public without restriction.

It has been found that the invention's rubella spike constructs are expressed and secreted in *Drosophila* S2 cells in such a way that they perfectly mimic the antigenic properties of the native heterodimeric rubella E2/E1 spikes, i.e. they depict (reveal, represent) them almost identical or at least in a way that the native virus does in diagnostic tests for the detection of IgM and IgG antibodies.

In principle, the production of rubella spike constructs using recombination techniques is not limited to the expression system of stably (permanently) or transiently (temporarily) transfected *Drosophila* S2 cells, but can also be performed using other eukaryotic expression systems such as the baculovirus expression system.

When using stably (permanently) or transiently (temporarily) transfected *Drosophila* S2 cells as expression system, the preferred signal sequence provided in the rubella spike construct is preferably the *Drosophila*-BiP signal sequence. This has proven to be particularly suitable in practice. Other functionally analogous *Drosophila* signal sequences can also be considered.

If other expression systems are used, other signal sequences may be necessary and/or more advantageous, e.g. the gp64 or HMS signal sequence in the case of the baculovirus expression system.

The invention also relates to a process for producing a soluble and immunoreactive rubella spike construct, the process comprising the following steps:
 (a) Cultivation of host cells, preferably *Drosophila* Schneider 2 (S2) cells;
 (b) Transforming the host cells with an expression vector comprising a nucleotide sequence encoding the rubella E1-E2 fusion protein in operative linkage;
 (c) Cultivation of the transfected host cells, whereby they express the rubella E1-E2 fusion protein (preferably continuously) and secrete the rubella spike constructs from the host cell;
 (d) Purification of the fusion protein.

The invention also relates to a method for the detection and/or determination and/or quantification of anti-rubella antibodies (in particular of the IgG or IgM subclasses or both) in a human sample, wherein the rubella spike construct is used as a capture reagent or binding partner or both for the anti-rubella antibodies.

In principle, all biological fluids known to the expert are suitable as samples.

The invention further comprises a reagent kit (test kit) for carrying out this method for the detection of anti-rubella antibodies, said kit containing at least one rubella spike construct as antigen.

The rubella spike construct as antigen can be used as a specific conjugate for the selective detection of bound anti-rubella IgM antibodies, especially when used in a so-called "μ-capture ELISA". For this purpose, the rubella spike construct can be provided with different tags (e.g. His6 tag, (Twin)-Strep tag or other tags) and thus the antigen can be specifically and optimally designed for the production of conjugates (enzymatic label, fluorophores, etc.). The economic efficiency of conjugate production is thus significantly improved. Frequently used non-selective chemical conjugation methods, such as crosslinking of proteins with glutardialdehyde, can be replaced by such intrinsic directed coupling with high efficiency and reproducibility.

The rubella spike construct according to the invention is highly soluble and immunologically highly reactive (synonym: highly antigenic), i.e. it is very well able to bind to or be recognized and bound by antibodies specific for rubella (e.g. in the case of anti-rubella El antibodies in a sample). It is therefore very well suited as an antigen for diagnostic applications. It offers a full-fledged replacement for the antigens from whole virus, which are used in different diagnostic platforms (ELISA, particles, etc.) according to the state of the art.

The main advantages are, that there is no biohazard due to potentially infectious material during production, that production takes place under S1 conditions according to GenTG (abbreviation for Gentechnikgesetz, i.e. the German Genetic Engineering Law), and that an increased yield and improved standardization of production compared to the state of the art is achieved by monoclonalization of *Drosophila* S2 cells as an expression system.

Further important advantages are a cost-efficient production by using modern biotechnological processes such as bioreactors (batch or perfusion) and the production in serum-free media i.e. by eliminating potentially infectious proteins (e.g. pathologically modified prions as in the case of BSE) or immunogenic proteins from used animal components such as especially FCS or BSA. Both advantages offer future security in the production and application of the antigen under ethical as well as regulatory aspects.

Due to the basically unlimited manipulability of the components of the rubella spike construct, adaptations to new technological requirements can be made relatively easily. For example, tags of all kinds can be introduced for directional coupling on a wide variety of surfaces, and the preparation of conjugates for μ-capture tests on different platforms (ELISA, CLIA, fluorescence-labelled conjugates) can also be realized without major technical difficulties. Since the rubella spike construct according to the invention depicts (reveals, represents) the native heterodimeric rubella E2/E1 spikes in practically the same way as the native virus in diagnostic tests, it is basically suitable for the detection of any kind of anti-rubella antibodies (especially IgM, IgG and IgA) in diagnostic (especially serological) tests.

Investigations by immunodiagnostic tests on the immunological reactivity of rubella spike constructs as antigens compared to state of the art rubella antigens show that the invented rubella spike construct antigens are well suited for use in diagnostic test systems for rubella IgM and -IgG serology across platforms. With regard to the standard antigens currently used in the state of the art, namely the isolated whole rubella virus, this represents a significant improvement because the rubella spike constructs according to the invention can be modified almost arbitrarily ("tailor-made antigens") and adapted to existing and future diagnostic procedures and requirements in rubella serology. In addition, the invention's rubella spike construct antigens enable a more cost-effective production and a significantly improved product and quality consistency compared to the previous standard antigen whole-virus via biotechnological production as recombinant proteins. In addition, it can be assumed that the in principle almost unlimited manipulability of the rubella spike construct protein (e.g. size of the epitopes, composition of the epitopes, etc.) allows a targeted elimination of interfering influences such as cross-reactivity or unspecific reactions, and this across platforms, individually for each serological application in rubella serology.

Due to the improved quality and quantity of accessible native-like conformational epitopes, the rubella spike construct is also a promising candidate for a broadly applicable vaccine against rubella infections.

The invention also concerns the use of the rubella spike construct as a vaccine. Thus, the subject of the invention is also a vaccine preparation comprising the rubella spike construct as an antigenic agent.

The production of vaccines containing an immunogenic polypeptide as the active ingredient is known to experts. Such vaccines are usually provided as injectable preparations (liquid solutions or suspensions). The active ingredient, here the rubella spike construct, is mixed with excipients that are pharmaceutically acceptable and compatible with the active ingredient (e.g. water, aqueous physiological buffers, saline solution, dextrose, glycerol, ethanol).

The invention is explained in more detail in the following on the basis of design examples and illustrations.

SHORT DESCRIPTION OF THE ILLUSTRATIONS

FIG. 1: Models of the glycoprotein E2/E1 spike configuration.

(A) Configuration of the glycoproteins E2 and E1 on the surface of a native rubella virus.

(B) Configuration of the soluble rubella spike constructs. In these constructs the transmembrane regions and the intravirional domains (light grey lines) are removed and the ectodomains of E1 and E2 (black lines) are connected by a flexible glycine-serine linker.

FIG. 2 amino acid sequence of the rubella spike construct;

(A) rubella spike construct "long" (i.e. with long linker)

(B) rubella spike construct "short" (i.e. with short linker)

Smooth underline: BiP signal sequence

Bright gray background: Amino acid sequence of the E2 fragment

Punctured Underlined: Glycine-serine linker short (8 amino acids)

White background: Amino acid sequence of the E1 fragment

FIG. 3: Characterization of rubella spike constructs on SDS-PAGE:

Aliquots of the purified rubella spike constructs ("short" and "long") after separation by SDS-PAGE (4-20% tris-glycine gels, article number TG 42010, Anamed Elektrophoresis GmbH) under reducing conditions and subsequent staining with Coomassie-Brillant-Blue.

Lane 1: Molecular weight marker (kDa),

Lane 2: Rubella spike construct "long",

Lane 3: Rubella spike construct "short".

Figure 4A:
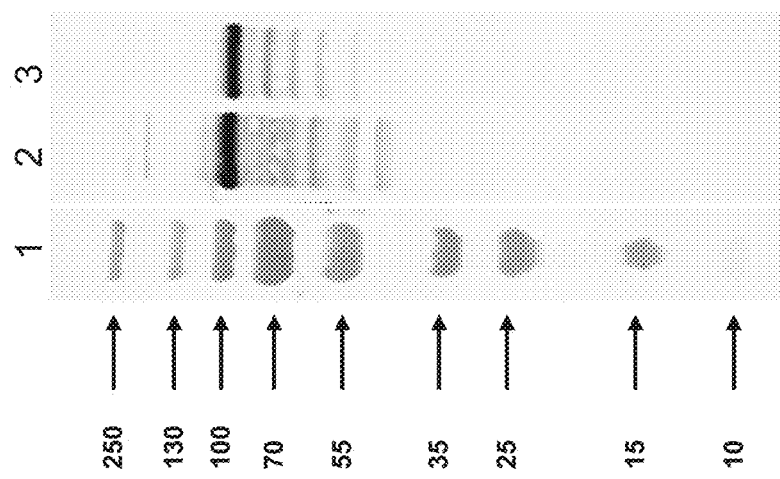
Figure 5:
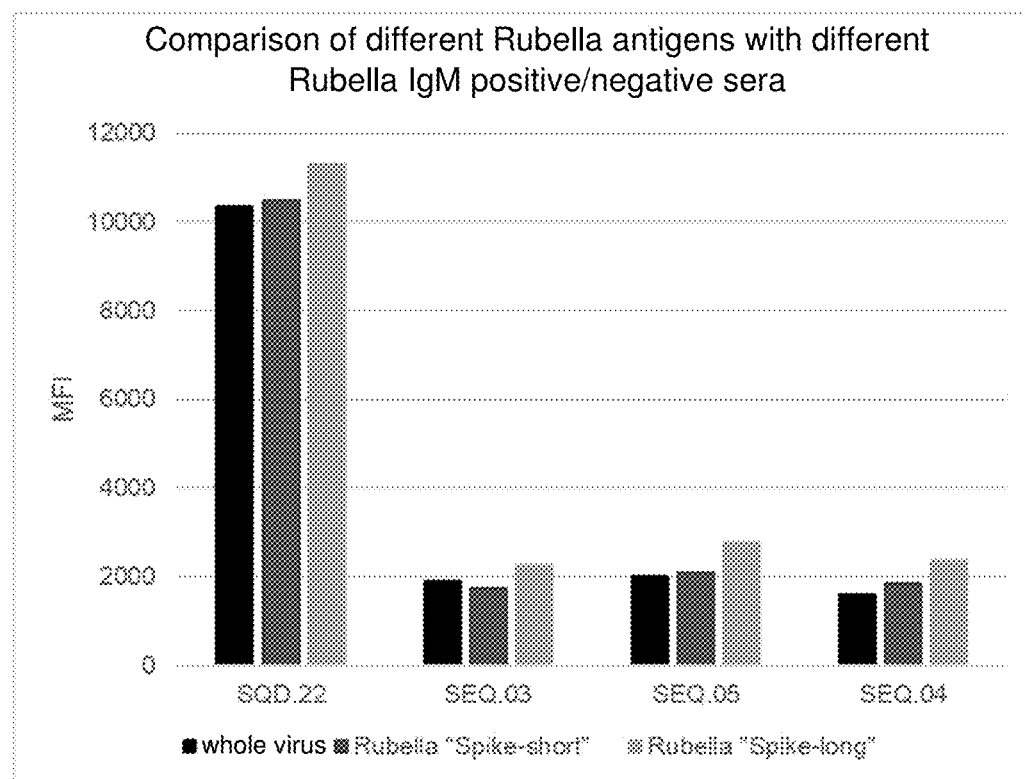
Figure 6:
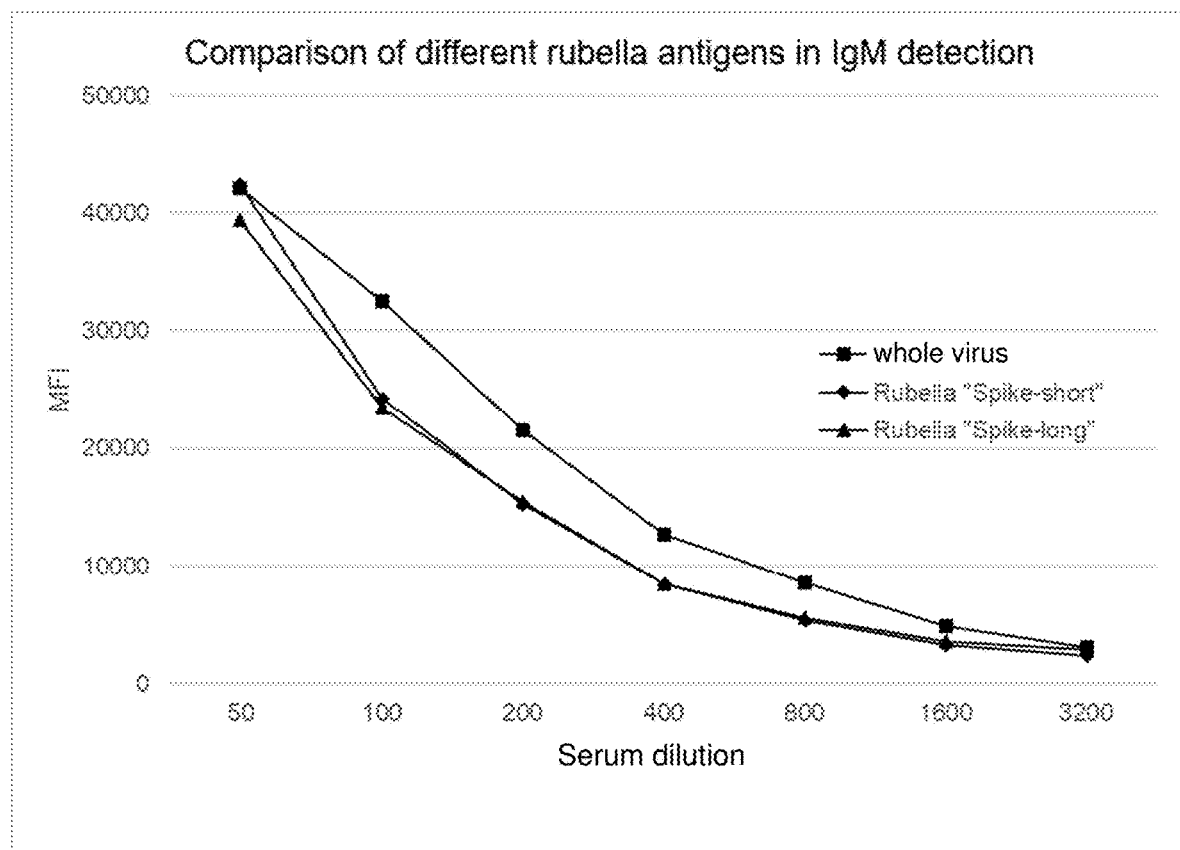
Figure 7:
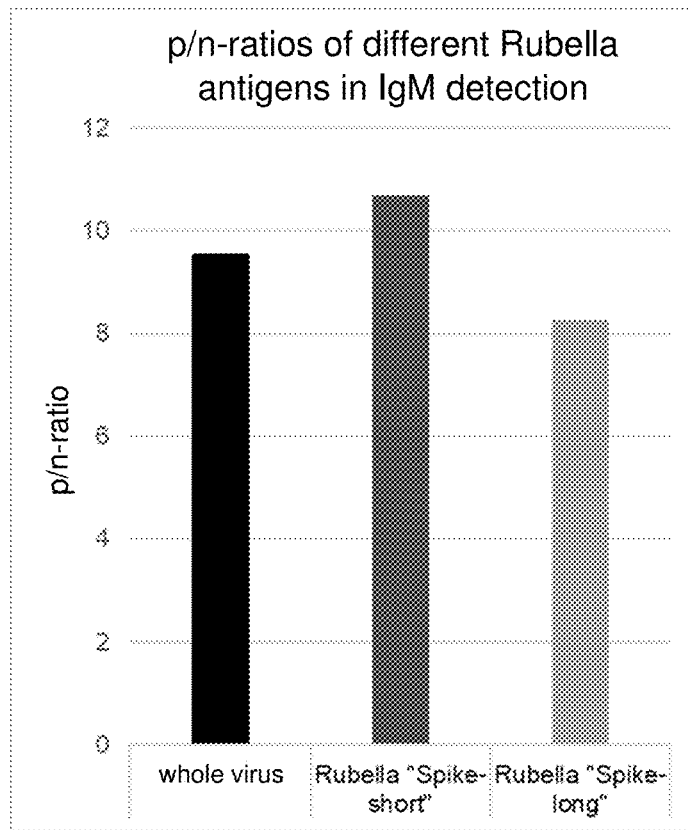
Figure 8C:
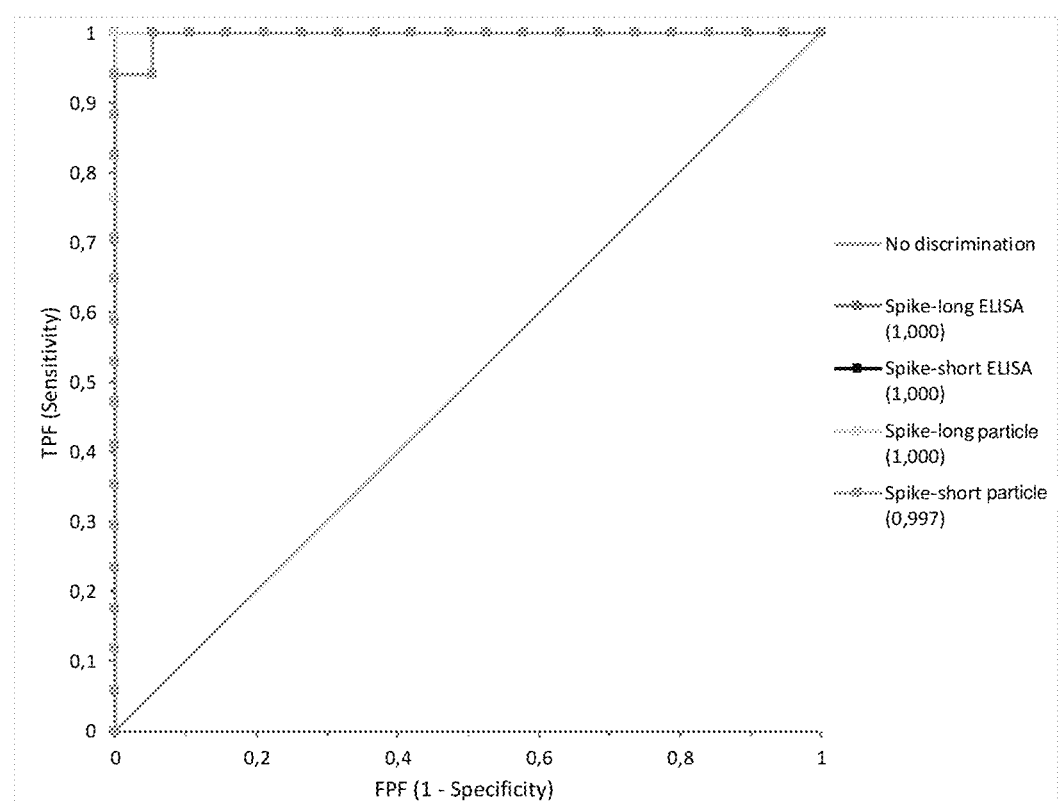
Figure 9C:
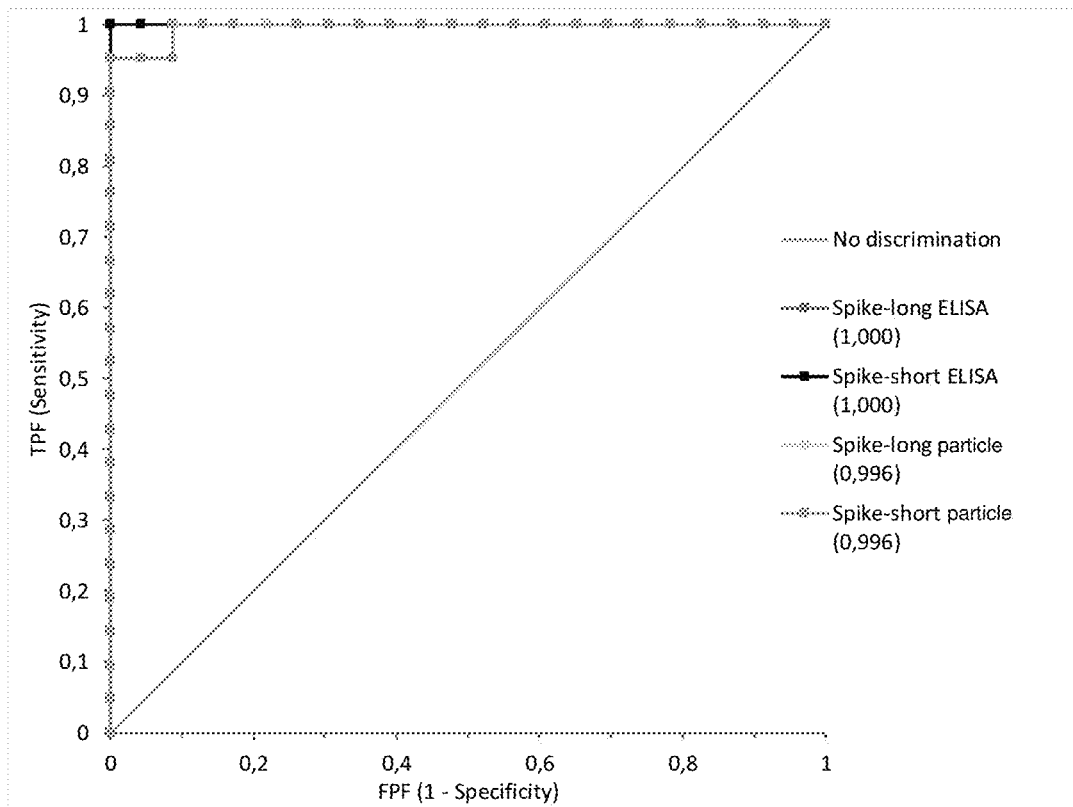

FIG. 4: Characterization of the rubella spike constructs in a Western blot:
Reaction of the rubella spike protein constructs purified by SDS-PAGE and then transferred to PVDF membrane with monoclonal antibodies directed either against rubella glycoprotein E1 (A) or rubella glycoprotein E2 (B).
(A): Antibody=Anti-rubella virus structural glycoprotein, monoclonal, mouse
(MABR23-Ru6, ibt—immunological and biochemical testsystems GmbH).
Lane 1: Molecular size marker (kDa),
Lane 2: Rubella spike construct "long",
Lane 3: Rubella spike construct "short".
(B): Antibody=Anti-rubella Virus E2 monoclonal antibody (D92G)
(MA5-18255, Thermo Fisher Scientific).
Lane 1: Molecular weight marker (kDa),
Lane 2: Rubella spike construct "long",
Lane 3: Rubella spike construct "short".
FIG. 5 Immunological reactivity of different rubella spike constructs (as antigens) compared to whole virus—in particle test with different rubella IgM positive/negative human sera.
x-axis: Human sera
y axis: MFI=Mean fluorescence intensity
FIG. 6 Immunological reactivity of different rubella spike constructs (as antigens) compared to whole virus—titration behaviour in the particle test with a selected, for rubella IgM positive, high titre human serum.
FIG. 7 Immunological reactivity of different rubella spike constructs (as antigens) compared to whole virus—p/n (positive/negative) ratio in particle-based detection of rubella IgM antibodies in different human sera.
FIGS. 8A-8C Immunological reactivity of different rubella spike constructs as antigens in an immunodiagnostic test—detection of anti-rubella IgM antibodies in selected, pre-characterized anti-rubella IgM human sera compared to a whole virus based reference test (ELISA).
FIGS. 8A and 8B: Table of values
ID: Sample identification
OD: Optical density at 405 nm
MFI: Mean fluorescence intensity
pos: Positive rating for anti-rubella IgM antibodies
neg: Negative rating for anti-rubella IgM antibodies
FIG. 8B is the continuation of table FIG. 8A in vertical direction.
FIG. 8C: Diagnostic performance (diagnostic efficiency)
ROC (receiver operating characteristic) curve.
FIGS. 9A-9C: Immunological reactivity of different rubella spike constructs as antigens in an immunodiagnostic test—detection of anti-rubella IgG antibodies in selected, pre-characterized anti-rubella IgG human sera compared to a whole virus based reference test (ELISA).
FIGS. 9A and 9B: Table of values
ID: Sample identification
OD: Optical density at 405 nm
MFI: Mean fluorescence intensity
pos: Positive rating for anti-rubella IgG antibodies
neg: Negative rating for anti-rubella IgG antibodies
FIG. 9B is the continuation of table FIG. 9A in vertical direction.
FIG. 9C: Diagnostic performance
ROC (receiver operating characteristic) curve EXAMPLE 1: GENERATION OF THE SOLUBLE RECOMBINANT RUBELLA SPIKE CONSTRUCTS ACCORDING TO THE INVENTION The production of the rubella spike constructs according to the invention is principally carried out in such a way that according to the schematic illustration in FIG. 1 the transmembrane region and the intravirional domain of the E2 glycoprotein and the C-terminal transmembrane region of the E1 glycoprotein are removed and the ectodomains of E1 and E2 are connected (coupled) to each other by a flexible glycine-serine linker.

In a concrete exemplary design, in which the rubella spike constructs according to the invention are derived from the glycoproteins E1 and E2 from the rubella strain M33, the C-terminus of the ectodomain of E2 (amino acids 1-234 of E2 according to SEQ ID NO:8) is connected to the N-terminus of the ectodomain of E1 (amino acids 1-446 of E1 according to SEQ ID NO:6) via a short linker (rubella spike "short") or a long linker (rubella spike "long"). (Reference sequence see: UniProtKB/SwissProt—P08563 (POLS_RUBVM), version 2 of the sequence, sequence update May 30, 2006). The amino acid sequence of these rubella spike constructs is shown in FIG. 2A and SEQ ID NO:2 (rubella spike construct "long" i.e. with long linker) and in FIG. 2B and SEQ ID NO:4 (rubella spike construct "short" i.e. with short linker).

When deriving the rubella spike constructs according to the invention from the glycoproteins E1 and E2 from the rubella strain rubella TO-336 (RUBY) UniProtKB/SwissProt—P08564 (POLS_RUBVV) Version 3 of the sequence, Sequence Update May 30, 2006, which has a 99% amino acid sequence homology to strain M33, the construct is basically build in the same way.

For expression of the rubella spike construct in *Drosophila melanogaster* Schneider 2 (S2) cells, the protein construct should preferably be provided with a BiP *Drosophila* signal sequence or a functionally analogous signal sequence at the N-terminus. The BiP *Drosophila* signal sequence promotes the secretion of the expressed rubella spikes from *Drosophila* S2 cells particularly well.

Production of rubella spikes is not restricted to stable or transient transfected *Drosophila* S2 cells. Other eukaryotic expression systems such as the baculovirus expression system may also be considered. When using other expression systems, other signal sequences may be required, e.g. the gp64 or HMS signal sequence for the baculovirus expression system.

In order to enable an effective purification of the expressed rubella spike constructs, the E1-E2 fusion protein C-terminal according to the invention is provided (coupled) with a streptavidin affinity tag in the present execution example.

Other affinity tags, e.g. a His tag, are also possible. The position of the affinity tag, too, is not restricted to the C-terminus of the E1-E2 fusion protein but can also be located at the N-terminus or in the linker.

(A) Production of the Nucleotide Sequence Encoding the Rubella Spike Constructs

The production of the nucleotide sequence coding for the invention's E1-E2 fusion protein of the rubella spike construct according to FIG. 1 (B) is preferably carried out using known rubella virus RNA sequences for the envelope proteins E1 and E2 deposited in sequence databases.

For example, for the above-mentioned rubella spike construct derived from rubella strain M33, a nucleotide sequence is used that is constructed based on the rubella virus 24S mRNA according to GenBank, Accession X05259, VersionX05259.1.

In detail, the following procedure is followed:

The production of the rubella spike constructs "short" (with short linker) and "long" (with long linker) is basically the same. Therefore, the following description of the manufacturing process, only refers to rubella spike construct.

The nucleotide sequence encoding the rubella spike construct (e.g. SEQ ID NO: 1 or SEQ ID NO: 3) is created synthetically, preferably supplemented with an affinity tag sequence, and cloned into a standard pMX cloning vector (Invitrogen/Geneart, Regensburg). It is codon-optimized for expression in *Drosophila melanogaster* and contains a Kozak sequence (gccaccATG) to ensure an efficient start of translation during protein biosynthesis in *Drosophila* S2 cells. In addition, the DNA construct contains an EcoRI and a NotI restriction site for the purpose of cloning the rubella spike DNA construct into the expression vector pExpres2.1 (see EP2307543B1; commercially available from Expres2ion Biotechnologies, Horsholm, Denmark).

(B) Production of the Transfection Vector for Recombinant Protein Production

Nucleotide sequences produced according to (A), which encode rubella spike constructs,—here for example rubella spike constructs derived from rubella strain M33 (e.g. SEQ ID NO:1 or SEQ ID NO:3)—, are cloned into a transfection vector suitable for the cells of the intended cell culture system.

As cell culture system especially *Drosophila melanogaster* Schneider 2 (S2) cells are considered. A suitable transfection vector for these cells is the *Drosophila* S2 expression vector pExpres2.1 (commercially available from Expres2ion Biotechnologies, Horsholm, Denmark; see also EP2307543B1). The pExpres2.1 expression vector contains the Zeocin resistance gene as selection marker.

For expression in *Drosophila* (S2) cells according to the present execution example, the nucleotide sequence produced according to example (A) (coding for the rubella spike constructs) was inserted into the expression vector pExpres2.1.

The necessary cloning steps were performed according to pExpres2.1 manufacturer's instruction and are generally known and familiar to the expert.

*Drosophila* S2 cells were transfected with the generated transfection vector.

(C) Expression of Rubella Spike Constructs in *Drosophila* S2 Cell Cultures

*Drosophila* S2 cells are cells from the embryonic Schneider 2 cell line *Drosophila melanogaster*, which are deposited with and can be obtained from DSMZ—Deutsche Sammlung von Mikroorganismen and Zellkulturen GmbH, InhoffenstraBe 7 B, 38124 Braunschweig, Germany, under depot number DSMZ ACC 130, and with the American Type Culture Collection (ATCC), P.O. Box 1549, Manassas, Va. 20108, USA, under depot number CRL-1963.

The *Drosophila* S2 cells used in the execution example described here originate from cell cultures of the company Expres2ion Biotechnologies, Horsholm, Denmark, they are commercially available as so-called "ExpreS$^2$ cells", and they are referred to as "S2 cells" in the following.

Used Materials:
Fetal Calf Serum "FCS"
Serum-free medium for insect cells, e.g. EX-CELL® 420 (article number 14420, Sigma)
Zeocin (article number R25001, Thermo Fisher Scientific)
Penicillin-Streptomycin, 10,000 U/ml Penicillin, 10 mg/ml Streptomycin (article number P06-07050, PAN Biotech)
(*Drosophila melanogaster*) S2 cells (ExpreS$^2$ cells, Expres2ion Biotechnologies)
ExpreS$^2$ Insect-TRx5 Transfection Reagent (article number S2-55A-001, Expres2ion Biotechnologies)
Buffer W: 100 mM Tris/HCl pH 8.0, 150 mM NaCl, 1 mM EDTA
Buffer E: 100 mM Tris/HCl pH 8.0, 150 mM NaCl, 1 mM EDTA, 2.5 mM Desthiobiotin
BioLock-Biotin Blocking Solution (article number 2-0205-050, IBA Lifesciences)
Cell culture flasks with Filter Cap, 25 cm$^2$ (T-25) (article number 156367, Thermo Fisher Scientific)
Cell culture flasks with Filter Cap, 80 cm2 (T-80) (article number 178905, Thermo Fisher Scientific)
Shaker bottle with filter cap, 250 mL (article number 431144, Corning) (working volume: 20-60 mL)
Roller bottle, PET 850 cm$^2$ (article number 680180, Greiner bio-one GmbH) with ventilation cap (article number 383382, Greiner bio-one GmbH) (working volume: 200-400 mL)
Cryotubes with female thread (article number 114841, Brand GmbH)
Cell counting chamber, Neubauer Improved (Brand GmbH)
Shaking incubator (CERTOMAT BS-1, Sartorius Stedim Biotech)
TFF membrane, Vivaflow 200, 10,000 MWCO Hydrosart Membrane (article number VF20H0, Sartorius Stedim Biotech)
Filter (0.45 µm), Minisart (article number 16555-K, Sartorius Stedim Biotech)
Äkta-pure chromatography system (GE Healthcare)
Strep-Tactin® Superflow® high capacity cartridge, 5 mL (article number 2-1238-001, IBA Lifesciences)

(i) Transfection and Production of a Stably Transformed *Drosophila* S2 Cell Line To generate the stably transformed S2 cell line, the pExpres2-1 expression vectors produced according to (B) are transfected into the S2 cells with the inserts coding for the rubella spike constructs ("short" or "long"). For this purpose, the S2 cells of the shaker bottle are counted and adjusted to 2×10$^6$ cells/mL in EX-CELL420 medium. Per transfection 5 mL of this cell suspension are transferred into a T-25 cell culture flask. Then 50 µL of transfection reagent is added and the transfection reagent is evenly distributed in the medium by tilting the bottle. Plasmid DNA (preferably 5-15 µg) is then added and evenly distributed by tilting the bottle. The T-25 bottle is incubated at 23-27° C. After about 3-4 hours 1 mL FCS is added.

After 2 days the selection phase is initiated by adding Zeocin up to a final concentration of about 1500-2000 µg/mL. The cells are counted every 3-4 days. As soon as their concentration is higher than 1×10$^6$ cells/mL, the cells are diluted in fresh selection medium (EX-CELL420+10% FCS and Zeocin (final concentration about 1500-2000 µg/mL)) to 1×10$^6$ cells/mL in a final volume of 6 mL. This procedure is repeated several times at intervals of several days. After 2-4 weeks of selection in medium containing Zeocin, the cell line can be considered stable. Following the selection phase and as soon as the cells have reached a concentration of >6×10$^6$ cells/mL, 6 mL of this cell suspension are transferred from the T-25 to a T75 bottle containing 4 mL fresh medium (EX-CELL420+10% FCS). Once these cells have recovered, 5 mL of fresh medium (EX- CELL420+10% FCS) is added again. The cells are counted after 3-4 days. As soon as the cells have reached a concentration of >6×10$^6$ cells/mL, 15 mL of these cells are transferred to a 250 mL shaker bottle and 15 mL medium (EX-CELL420) is added. The cells are expanded as described in (ii).

(ii) Expansion of *Drosophila* S2 Cells in Shaking Flasks

The S2 cell culture prepared according to (i) is maintained and monitored in the expansion process. As soon as the viability of the cells is >90% and the cell concentration>8× 10$^6$ cells/mL, the cells are diluted in EX-CELL420 medium to 8×10$^6$ cells/mL. If the total volume of the culture does not exceed the allowable working volume of the shaking flask, the fresh medium of the original flask is simply added for this purpose. If the total volume would exceed the allowable working volume of the original bottle, the cells are diluted to 8×10$^6$ cells/mL and distributed to several shaking flasks. Typically, the cells are diluted every 3-4 days. After 3-4 days a cell concentration of 25-50×10$^6$ cells/mL is typically reached.

(iii) Production of the Rubella Spike Constructs

For the production and recovery of the rubella spike constructs, the polyclonal cell lines obtained according to (i) or (ii) shall be cultivated in serum-free medium. After approximately four days of cultivation the cells are removed by centrifugation and the supernatant is harvested. Rubella spike constructs are isolated from the supernatant by affinity chromatography over Strep-Tactin columns using their C-terminal Streptavidin affinity tag labelling.

In detail, the following procedure is used for example:

The cell density of the cell suspension obtained in (i) or (ii) is adjusted to 8×$10^6$ cells/mL and the cells are transferred to a roller bottle (with vent cap) with the addition of penicillin-streptomycin (1:000). The roller bottles are incubated upright in a shaking incubator at 27° C. and 120 rpm for 4 days. Then the cells are separated and removed by centrifugation (4,400×g, 20 min). The cell supernatant is first concentrated by tangential flow filtration (Vivaflow 200, 10,000 MWCO Hydrosart membrane) to 1/10 of the initial volume and then continuously diafiltered with the same membrane against ten times the volume of buffer W. PMSF (final concentration 1 mM) is added to inhibit proteases in the concentrated cell supernatant. To remove biotin from the concentrated cell supernatant, a BioLock biotin blocking solution (3 mL/L) is added, incubated for 15 min with stirring at room temperature and then centrifuged (10,000×g, 30 min, 4° C.). The supernatant is filtered with a 0.45 μm filter. For purification of the strep-tagged rubella spike constructs, the supernatant is loaded onto a Strep-Tactin Superflow column of an Akta-pure chromatography system. After application, the supernatant is washed with 4 column volume buffer W and then eluted with 5 column volume buffer E. The obtained eluate is collected in several separate fractions. The fractions containing the rubella spike construct are combined and a protein concentration determination (e.g. according to Bradford) is performed.

EXAMPLE 2: CHARACTERIZATION OF THE ANTIGENIC PROPERTIES OF RUBELLA SPIKE CONSTRUCTS USING SDS-PAGE AND WESTERN BLOT

Aliquots of the rubella spike constructs "short" and "long" purified according to example 1 are applied to SDS-PAGE (4-20% tris-glycine gels, article number TG 42010, Anamed Elektrophorese GmbH), separated under reducing conditions and then stained with Coomassie brilliant blue. The results are shown in FIG. 3. The comparison with the molecular weight marker bands (kDa) in lane 1 shows that rubella spike construct "long" (lane 2) and rubella spike construct "short" (lane 3) have molecular sizes of about 80 kDa. These values correspond to the molecule sizes that can be expected mathematically based on their amino acid sequence, namely 77 kDa for rubella spike construct "long" and 76 kDa for rubella spike construct "short".

For the Western blot, the proteins from the SDS-PAGE are transferred to a PVDF membrane. After blocking free protein binding sites, the proteins on the membrane are incubated with a monoclonal antibody for rubella glycoprotein E1 and a monoclonal antibody for rubella glycoprotein E2. The antibodies used are for example (a) anti-rubella virus structural glycoprotein, monoclonal, mouse (MABR23-Ru6, ibt—immunological and biochemical testsystems GmbH), which reacts with glycoprotein E1, and (b) rubella virus E2 monoclonal antibody (D92G) (MA5-18255, Thermo Fisher Scientific), which reacts with glycoprotein E2. For visualization, incubation with an anti-mouse IgG antibody from goat (alkaline phosphatase conjugate) is subsequently carried out. The results of the Western blots are shown in FIGS. 4 (A) and (B). The comparison with the molecular weight marker bands (kDa) in lane 1 shows that both the rubella spike construct "long" (lane 2) and the rubella spike construct "short" (lane 3) are recognized by the anti-rubella E1 and anti-rubella E2-antibodies. These results clearly show that epitopes of rubella glycoprotein E1 and rubella glycoprotein E2 are present in both the "long" and "short" constructs.

EXAMPLE 3: INVESTIGATION OF IMMUNOLOGICAL REACTIVITY OF RUBELLA SPIKE CONSTRUCTS IN IMMUNODIAGNOSTIC TEST: DETECTION OF ANTI-RUBELLA IGM ANTIBODIES IN HUMAN SERA

Two different test systems were used—a conventional ELISA system and a particle-based system based on flow cytometry and a fluorescence read-out of the conjugate signal. Both systems (ELISA and particle-based) are representative systems (antigen carrier—particle or plate) for detection methods currently used in rubella IgM and IgG serology.

For the investigation of immunological reactivity of rubella spike constructs with respect to patient IgM antibodies, different test runs were performed, each in comparison to the whole virus (as the antigen commonly used in state-of-the-art technology):

(a) A particle test with four different human sera (i.e. sera from four different patients) yielded the results shown graphically in FIG. 5. The mean fluorescence intensity (MFI) on the y-axis is a measure of the amount of detected patient IgM antibodies in each sample. The results demonstrate that the rubella spike constructs "short" and "long" according to the invention at least match the detection performance of the whole virus, in most cases they even exceed it.

(b) A particle test with different dilutions of a selected human serum positive for rubella IgM and with high titre gave the results shown graphically in FIG. 6. The mean fluorescence intensity (MFI) on the y-axis is a measure of the amount of detected patient IgM antibodies in the respective dilution of the sample (x-axis). The results demonstrate that with a human serum the rubella spike constructs "short" and "long" according to the invention show a very similar and even improved "titration behaviour" compared to the whole virus. This is an essential property of an antigen for a serological test.

(c) The positive-to-negative ratio (P/N) for the antigens rubella spike construct "long" and "short", each in comparison to the whole virus, was determined by means of known methods using a particle-based in-house procedure and using different human sera positive and negative for rubella IgM. For each antigen or test setup the corresponding positive to negative ratio (P/N) was determined. The results are shown graphically in FIG. 7. They demonstrate that in a serological test for the detection of rubella IgM antibodies, the rubella spike constructs "short" and "long" according to the invention have a positive-to-negative ratio (P/N) that is very similar to that of the whole virus and in some cases superior to that of the whole virus. The positive-to-negative ratio (P/N) of a diagnostic test is, like the titration behaviour, an essential parameter of this test procedure and a measure of the so-called diagnostic performance: the higher the P/N ratio, the higher or better the diagnostic performance (d) In an additional comparative test, the two different test systems ELISA and particle-based system were used to investigate the immunological reactivity of the rubella spike constructs "short" and "long" with respect to anti-rubella IgM antibodies in 36 pre-characterized (i.e. pre-analysed for anti-rubella IgM antibodies) human serum samples, 17 positive and 19 negative. A whole-virus coated ELISA was used as reference.

To compare and determine the cut-off values for the experimental setups, a ROC analysis was performed in Microsoft Excel using the software "Analyse-it" (Analyse-it Software, Ltd., UK). The test results are shown in tabular and graphical form in FIGS. 8A-8B and FIG. 8C.

From FIGS. 8A-8B and FIG. 8C it can be seen that the new rubella spike construct antigens "short" and "long" can be successfully used for the serological differentiation of rubella IgM positive and rubella IgM negative patient samples in the ELISA setup as well as in the particle-based test. With both rubella spike construct antigens ("short" and/or "long") a clear differentiation of positive and negative samples from/in different donor collectives (panel) is possible. In comparison to the reference test (ELISA), sensitivities and specificities of 100% were achieved with the rubella spike construct "long" on both test platforms. With the rubella spike construct "short", sensitivities and specificities of 100% were also achieved in the ELISA. In the particle-based test, the sensitivity was 94.1% and the specificities were again 100%.

EXAMPLE 4: INVESTIGATION OF IMMUNOLOGICAL REACTIVITY OF RUBELLA SPIKE CONSTRUCTS IN IMMUNODIAGNOSTIC TEST: DETECTION OF ANTI-RUBELLA IGG ANTIBODIES IN HUMAN SERA

As in example 3, two different test systems were used—a conventional ELISA system and a particle-based system based on flow cytometry and on a fluorescence read-out of the conjugate signal.

For the investigation of the immunological reactivity of the rubella spike constructs "short" and "long" with respect to anti-rubella IgG antibodies, 44 pre-characterized (i.e. pre-analysed for anti-rubella IgG antibodies) human serum samples, 21 positive and 23 negative, were tested on both platforms against a commercial reference ELISA. The reference ELISA was coated with whole virus.

To compare and determine the cut-off values for the experimental setups, a ROC analysis was performed in Microsoft Excel using the software "Analyse-it" (Analyse-it Software, Ltd., UK). The test results are shown in tabular and graphical form in FIGS. 9A-9B and FIG. 9C.

FIGS. 9A-9B and FIG. 9C show that the new rubella spike construct antigens "short" and "long" can be successfully used for the serological differentiation of Rubella IgG positive and Rubella IgG negative patient samples in both ELISA setup and particle-based assays. With both rubella spike construct antigens ("short" and/or "long") a clear differentiation of positive and negative samples from/in different donor collectives (panel) is possible. In comparison to the reference test (ELISA), specificities of 100% were achieved with both rubella spike constructs "long" and "short" on both test platforms. The sensitivities of both constructs in the ELISA were also 100% in each case, in the particle-based test the sensitivity of both constructs was also 95.2% in each case.

NON-PATENT LITERATURE CITED

Battisti et al., 2012. Cryo-Electron Tomography of rubella Virus, J Virol. 2012 October; 86(20): 11078-11085.

DuBois et al., 2012. Functional and evolutionary insight from the crystal structure of rubella virus protein E1. Nature. 2013 Jan. 24; 493(7433):552-6.

Hobman et al., 1993: The rubella virus E2 and E1 spike glycoproteins are targeted to the Golgi complex. J. Cell Biol. 121: 269-281 (1993).

Hobman et al., 2007. Fields Virology Vol. 1 (ed. D. M Knipe) 1069-1100 (Lippincott Williams & Wilkins, 2007).

Katow et al., 1988. Low pH-induced conformational change of rubella virus envelope proteins. J Gen Virol 1988;69(pt 11):2797-2807.

Perrenoud G. et al. 2004: A recombinant rubella virus E1 glycoprotein as a rubella vaccine candidate. Vaccine 2004; 23(4):480-8.

Prasad et al., 2017. Assembly, maturation and three-dimensional helical structure of the teratogenic rubella virus. PLoS Pathog. 2017 Jun. 2; 13(6).

Schneider, I., 1972. Cell lines derived from late embryonic stages of *Drosophila melanogaster*. Journal of Embryology and Experimental Morphology 27 (2): 353-365. http://www.ncbi.nlm nih gov/pubmed/4625067.

Seppänen et al. 1991: Diagnostic potential of baculovirus-expressed rubella virus envelope proteins. Clin. Microbiol, 1991,1877-1882.

Waxham et al., 1985. Detailed immunologic analysis of the structural polypeptides of rubella virus using monoclonal antibodies. Virology 1985; 143:153-165.

The invention claimed is:

1. Rubella virus antigen, wherein it is a rubella virus E1-E2 envelope protein complex construct comprising
    at least one E1 component and one E2 component which are linked,
    wherein the E1 component consists of the E1 envelope protein whose C-terminal transmembrane region and intravirion are removed and whose N-terminus comprises the ectodomain of the E1 envelope protein,
    and wherein the E2 component consists of the E2 envelope protein whose transmembrane regions and intravirion are removed and whose N-terminus comprises the ectodomain of the E2 envelope protein,
    and wherein the C-terminus of the E2 component is connected to the N-terminus of the E1 component directly or by means of linkers.

2. The rubella virus antigen according to claim 1, wherein the antigen is produced as a recombinant E1-E2 fusion protein.

3. The rubella virus antigen of claim 2, wherein the E1-E2 fusion protein is coupled to a signal sequence.

4. The rubella virus antigen according to claim 1, wherein the E1-E2 fusion protein is coupled to an affinity tag.

5. The rubella virus antigen according to claim 1, wherein the ectodomain of the E1 envelope protein comprises the amino acids (of positions) 1-446 according to SEQ ID NO:6.

6. The rubella virus antigen according to claim 1, wherein the ectodomain of the E2 envelope protein comprises the amino acids (of positions) 1-234 according to SEQ ID NO:8.

7. The rubella virus antigen according to claim 1, wherein the linker is a flexible linker comprising glycine and/or serine.

8. The rubella virus antigen according to claim 2, wherein the fusion protein comprises the amino acid sequence according to SEQ ID NO: 2, wherein the signal sequence at the N-terminal end and/or the linker sequence in the middle region of this amino acid sequence is optionally present.

9. The rubella virus antigen according to claim 2, wherein the fusion protein comprises the amino acid sequence according to SEQ ID NO: 4, wherein the signal sequence at the N-terminal end and/or the linker sequence in the middle region of this amino acid sequence is optionally present.

10. A recombinant DNA molecule encoding a rubella virus antigen and comprising a nucleotide sequence encoding a rubella E1-E2 fusion protein according to claim 2.

11. The recombinant DNA molecule according to claim 10, wherein it comprises the nucleotide sequences according to SEQ ID NO: 5 and SEQ ID NO: 7.

12. The recombinant DNA molecule according to claim 10, wherein it comprises the nucleotide sequence according to SEQ ID NO: 1, wherein the signal sequence at the N-terminal end and/or the linker sequence in the middle region of this nucleotide sequence is optionally present.

13. The recombinant DNA molecule according to claim 10, wherein it comprises the nucleotide sequence according to SEQ ID NO: 3, wherein the signal sequence at the N-terminal end and/or the linker sequence in the middle region of this nucleotide sequence is optionally present.

14. An expression vector comprising a recombinant DNA molecule according to claim 10 in operative linkage.

15. An isolated host cell transformed with the expression vector according to claim 14.

16. The isolated host cell of claim 15, wherein it is an insect cell.

17. A process for preparing a rubella virus E1-E2 envelope protein complex construct according to claim 1, comprising the steps:
   (a) Cultivation of host cells;
   (b) Transfecting the host cells with an expression vector comprising a nucleotide sequence encoding the rubella E1-E2 fusion protein in operative linkage;
   (c) Cultivation of the transfected host cells, wherein said host cells express the Rubella E1-E2 fusion protein and secrete the Rubella spike constructs from the host cell;
   (d) Purification of the fusion protein.

18. A method for the qualitative and/or quantitative detection of anti-rubella antibodies in a liquid sample, the method comprising:
   providing the liquid sample; and
   using the rubella virus E1-E2 envelope protein complex construct according to claim 1 as capture reagent and/or binding partner for the anti-rubella antibodies.

19. A reagent kit (test kit) for carrying out a method for the qualitative and/or quantitative detection of anti-rubella antibodies in a liquid sample, wherein this kit contains at least one rubella virus E1-E2 envelope protein complex construct according to claim 1 as antigen.

20. A vaccine preparation comprising a rubella virus E1-E2 envelope protein complex construct according to claim 1 as the antigenic active ingredient.

* * * * *

SEQUENCE LISTING

<160> NUMBER OF SEQ ID NOS: 8

<210> SEQ ID NO 1
<211> LENGTH: 2112
<212> TYPE: DNA
<213> ORGANISM: Rubella virus

<400> SEQUENCE: 1

| | | | | | |
|---|---|---|---|---|---|
| ggactgcagc | cacgcgctga | tatggctgct | ccaccaatgc | caccacagcc | accacgtgct | 60 |
| cacggacagc | actacggaca | ccaccatcac | cagctgccat | ttctgggcca | cgatggacat | 120 |
| catggcggaa | cactgcgtgt | gggacagcat | caccgtaacg | ccagtgatgt | gctgccaggc | 180 |
| cattggttgc | aaggcggatg | gggctgctac | aacctgagcg | attggcacca | gggaacccac | 240 |
| gtgtgccaca | ccaagcacat | ggatttttgg | tgcgtggaac | acgatcgccc | gccaccagct | 300 |
| acaccaacca | gtctgacaac | agccgccaat | agcaccactg | ccgctacacc | agcaacagcc | 360 |
| ccaccaccat | gtcacgccgg | actgaatgat | agctgcggcg | gatttctgag | cggctgcgga | 420 |
| ccaatgcgtc | tgcgccatgg | tgctgataca | cgttgcggac | gcctgatttg | cggcctgagt | 480 |
| accaccgctc | agtaccccac | aacacgcttc | ggatgcgcta | tgcgttgggg | actgccacca | 540 |
| tgggaactcg | tggtgttgac | agcccgtcca | gaggatggat | ggacatgtcg | cggagtgcca | 600 |
| gctcatccag | gcacacgttg | tccagaactg | tgtccccaa | tgggacgtgc | cacatgtagt | 660 |
| ccagccagtg | ccttgtggct | ggccacagcc | aatgctttga | gtggcggaag | tggtggctca | 720 |
| ggcggatcag | gtggtggaag | tggcggagga | tctggaagcg | gaggcggtgg | cggagaagag | 780 |
| gcctttacct | acttgtgcac | agccccagga | tgcgccacac | agacacctgt | gccagttcgt | 840 |
| ctggctggcg | tgcgcttcga | gagcaagatt | gtggatggcg | gatgcttcgc | ccgtgggat | 900 |
| ctcgaagcta | ctggtgcctg | catctgcgag | atccccacag | atgtgtcctg | cgaaggactc | 960 |
| ggagcttggg | tgccaacagc | tccatgcgct | cgcatttgga | atggaaccca | gcgcgcctgc | 1020 |
| acattctggg | ccgtgaatgc | ttatagcagc | ggcggctatg | cccagctggc | ctcctacttt | 1080 |
| aatccaggcg | gcagctacta | caagcagtac | catccaaccg | cctgcgaggt | ggaaccagcc | 1140 |
| ttcggacata | gtgatgccgc | ctgctgggga | ttcccaaccg | atacagtgat | gagcgtgttc | 1200 |
| gccctggcca | gctacgtgca | gcatccacat | aagaccgtgc | gcgtgaagtt | ccacaccgag | 1260 |
| acacgtacag | tgtggcagtt | gagtgtggcc | ggcgtgtcct | gcaatgtgac | caccgaacat | 1320 |
| ccgttctgca | acacccccaca | cggccagttg | aaagtgcaag | tgccaccaga | tccaggcgat | 1380 |
| ctggtcgagt | acatcatgaa | ctacaccggc | aaccagcaga | gccgctgggg | actgggaagc | 1440 |
| ccaaattgcc | atggaccgga | ttgggcaagc | ccagtgtgcc | aacgtcatag | cccagattgc | 1500 |
| agtcgcctcg | tgggagccac | accagaacgt | ccacgtctgc | gtttggtgga | tgccgatgat | 1560 |
| ccactgctgc | gtactgctcc | aggaccaggc | gaagtgtggg | ttaccccagt | gattggaagc | 1620 |
| caggctcgca | agtgcggcct | gcatattcgt | gccggaccat | acggacatgc | caccgtggaa | 1680 |
| atgcccgagt | ggattcacgc | ccacaccacc | agcgatccat | ggcacccacc | aggaccactg | 1740 |
| ggcctgaagt | ttaagacagt | gcgcccagtg | gccttgccac | gagctttggc | tccaccacgt | 1800 |
| aatgtgcgag | tgaccggctg | ctaccagtgc | ggaacaccag | ctctggtgga | aggattggct | 1860 |
| cccgcggag | gcaattgtca | cctgacagtg | aatggcgagg | atgtgggcgc | tttcccaccg | 1920 |
| ggcaaatttg | tgacagccgc | cttgctgaat | accccgccac | cttaccaagt | gtcgtgcggc | 1980 |
| ggagaaagtg | atcgtgctag | cgcccgtgtg | atcgatccag | ctgctcagag | ttttaccggc | 2040 |
| gtggtgtacg | gcacccatac | cacagccgtt | agtgaaaccc | gtcagacctg | gccgaatgg | 2100 | gctgctgctc at                                                                                          2112

<210> SEQ ID NO 2
<211> LENGTH: 722
<212> TYPE: PRT
<213> ORGANISM: Rubella virus

<400> SEQUENCE: 2

Met Lys Leu Cys Ile Leu Leu Ala Val Val Ala Phe Val Gly Leu Ser
1               5                   10                  15

Leu Gly Gly Leu Gln Pro Arg Ala Asp Met Ala Ala Pro Pro Met Pro
            20                  25                  30

Pro Gln Pro Pro Arg Ala His Gly Gln His Tyr Gly His His His His
        35                  40                  45

Gln Leu Pro Phe Leu Gly His Asp Gly His His Gly Gly Thr Leu Arg
    50                  55                  60

Val Gly Gln His His Arg Asn Ala Ser Asp Val Leu Pro Gly His Trp
65                  70                  75                  80

Leu Gln Gly Gly Trp Gly Cys Tyr Asn Leu Ser Asp Trp His Gln Gly
                85                  90                  95

Thr His Val Cys His Thr Lys His Met Asp Phe Trp Cys Val Glu His
            100                 105                 110

Asp Arg Pro Pro Ala Thr Pro Thr Ser Leu Thr Thr Ala Ala Asn
        115                 120                 125

Ser Thr Thr Ala Ala Thr Pro Ala Thr Pro Pro Pro Cys His Ala
    130                 135                 140

Gly Leu Asn Asp Ser Cys Gly Gly Phe Leu Ser Gly Cys Gly Pro Met
145                 150                 155                 160

Arg Leu Arg His Gly Ala Asp Thr Arg Cys Gly Arg Leu Ile Cys Gly
                165                 170                 175

Leu Ser Thr Thr Ala Gln Tyr Pro Pro Thr Arg Phe Gly Cys Ala Met
            180                 185                 190

Arg Trp Gly Leu Pro Pro Trp Glu Leu Val Val Leu Thr Ala Arg Pro
        195                 200                 205

Glu Asp Gly Trp Thr Cys Arg Gly Val Pro Ala His Pro Gly Thr Arg
    210                 215                 220

Cys Pro Glu Leu Val Ser Pro Met Gly Arg Ala Thr Cys Ser Pro Ala
225                 230                 235                 240

Ser Ala Leu Trp Leu Ala Thr Ala Asn Ala Leu Ser Gly Gly Ser Gly
                245                 250                 255

Gly Ser Gly Gly Ser Gly Gly Ser Gly Gly Ser Gly Ser Gly
            260                 265                 270

Gly Gly Gly Glu Glu Ala Phe Thr Tyr Leu Cys Thr Ala Pro Gly
        275                 280                 285

Cys Ala Thr Gln Thr Pro Val Pro Val Arg Leu Ala Gly Val Arg Phe
    290                 295                 300

Glu Ser Lys Ile Val Asp Gly Gly Cys Phe Ala Pro Trp Asp Leu Glu
305                 310                 315                 320

Ala Thr Gly Ala Cys Ile Cys Glu Ile Pro Thr Asp Val Ser Cys Glu
                325                 330                 335

Gly Leu Gly Ala Trp Val Pro Thr Ala Pro Cys Ala Arg Ile Trp Asn
            340                 345                 350

Gly Thr Gln Arg Ala Cys Thr Phe Trp Ala Val Asn Ala Tyr Ser Ser
        355                 360                 365

Gly Gly Tyr Ala Gln Leu Ala Ser Tyr Phe Asn Pro Gly Gly Ser Tyr
        370                 375                 380

Tyr Lys Gln Tyr His Pro Thr Ala Cys Glu Val Glu Pro Ala Phe Gly
385                 390                 395                 400

His Ser Asp Ala Ala Cys Trp Gly Phe Pro Thr Asp Thr Val Met Ser
            405                 410                 415

Val Phe Ala Leu Ala Ser Tyr Val Gln His Pro His Lys Thr Val Arg
            420                 425                 430

Val Lys Phe His Thr Glu Thr Arg Thr Val Trp Gln Leu Ser Val Ala
            435                 440                 445

Gly Val Ser Cys Asn Val Thr Thr Glu His Pro Phe Cys Asn Thr Pro
    450                 455                 460

His Gly Gln Leu Glu Val Gln Val Pro Pro Asp Pro Gly Asp Leu Val
465                 470                 475                 480

Glu Tyr Ile Met Asn Tyr Thr Gly Asn Gln Gln Ser Arg Trp Gly Leu
                485                 490                 495

Gly Ser Pro Asn Cys His Gly Pro Asp Trp Ala Ser Pro Val Cys Gln
            500                 505                 510

Arg His Ser Pro Asp Cys Ser Arg Leu Val Gly Ala Thr Pro Glu Arg
            515                 520                 525

Pro Arg Leu Arg Leu Val Asp Ala Asp Asp Pro Leu Leu Arg Thr Ala
    530                 535                 540

Pro Gly Pro Gly Glu Val Trp Val Thr Pro Val Ile Gly Ser Gln Ala
545                 550                 555                 560

Arg Lys Cys Gly Leu His Ile Arg Ala Gly Pro Tyr Gly His Ala Thr
                565                 570                 575

Val Glu Met Pro Glu Trp Ile His Ala His Thr Thr Ser Asp Pro Trp
            580                 585                 590

His Pro Pro Gly Pro Leu Gly Leu Lys Phe Lys Thr Val Arg Pro Val
            595                 600                 605

Ala Leu Pro Arg Ala Leu Ala Pro Pro Arg Asn Val Arg Val Thr Gly
    610                 615                 620

Cys Tyr Gln Cys Gly Thr Pro Ala Leu Val Glu Gly Leu Ala Pro Gly
625                 630                 635                 640

Gly Gly Asn Cys His Leu Thr Val Asn Gly Glu Asp Val Gly Ala Phe
                645                 650                 655

Pro Pro Gly Lys Phe Val Thr Ala Ala Leu Leu Asn Thr Pro Pro Pro
            660                 665                 670

Tyr Gln Val Ser Cys Gly Gly Glu Ser Asp Arg Ala Ser Ala Arg Val
            675                 680                 685

Ile Asp Pro Ala Ala Gln Ser Phe Thr Gly Val Val Tyr Gly Thr His
    690                 695                 700

Thr Thr Ala Val Ser Glu Thr Arg Gln Thr Trp Ala Glu Trp Ala Ala
705                 710                 715                 720

Ala His

<210> SEQ ID NO 3
<211> LENGTH: 2064
<212> TYPE: DNA
<213> ORGANISM: Rubella virus

<400> SEQUENCE: 3
ggactgcagc cacgcgctga tatggctgct ccaccaatgc caccacagcc accacgtgct    60

-continued

| | |
|---|---|
| cacggacagc actacggaca ccaccatcac cagctgccat ttctgggcca cgatggacat | 120 |
| catggcggaa cactgcgtgt gggacagcat caccgtaacg ccagtgatgt gctgccaggc | 180 |
| cattggttgc aaggcggatg gggctgctac aacctgagcg attggcacca gggaacccac | 240 |
| gtgtgccaca ccaagcacat ggattttggg tgcgtggaac acgatcgccc gccaccagct | 300 |
| acaccaacca gtctgacaac agccgccaat agcaccactg ccgctacacc agcaacagcc | 360 |
| ccaccaccat gtcacgccgg actgaatgat agctgcggcg gatttctgag cggctgcgga | 420 |
| ccaatgcgtc tgcgccatgg tgctgataca cgttgcggac gcctgatttg cggcctgagt | 480 |
| accaccgctc agtacccacc aacacgcttc ggatgcgcta tgcgttgggg actgccacca | 540 |
| tgggaactcg tggtgttgac agcccgtcca gaggatggag gacatgtcg cggagtgcca | 600 |
| gctcatccag gcacacgttg tccagaactg gtgtccccaa tggacgtgc cacatgtagt | 660 |
| ccagccagtg ccttgtggct ggccacagcc aatgctttga gtggcggaag tggtggctca | 720 |
| ggcggagaag aggcctttac ctacttgtgc acagccccag gatgcgccac acagacacct | 780 |
| gtgccagttc gtctggctgg cgtgcgcttc gagagcaaga ttgtggatgg cggatgcttc | 840 |
| gccccgtggg atctcgaagc tactggtgcc tgcatctgcg agatccccac agatgtgtcc | 900 |
| tgcgaaggac tcggagcttg ggtgccaaca gctccatgcg ctcgcatttg aatggaacc | 960 |
| cagcgcgcct gcacattctg ggccgtgaat gcttatagca gcggcggcta tgcccagctg | 1020 |
| gcctcctact ttaatccagg cggcagctac tacaagcagt accatccaac cgcctgcgag | 1080 |
| gtggaaccag ccttcggaca tagtgatgcc gcctgctggg gattcccaac cgatacagtg | 1140 |
| atgagcgtgt tcgccctggc cagctacgtg cagcatccac ataagaccgt gcgcgtgaag | 1200 |
| ttccacaccg agacacgtac agtgtggcag ttgagtgtgg ccggcgtgtc ctgcaatgtg | 1260 |
| accaccgaac atccgttctg caacaccca cacggccagt ggaagtgca agtgccacca | 1320 |
| gatccaggcg atctggtcga gtacatcatg aactacaccg gcaaccagca gagccgctgg | 1380 |
| ggactgggaa gcccaaattg ccatggaccg gattgggcaa gcccagtgtg ccaacgtcat | 1440 |
| agcccagatt gcagtcgcct cgtgggagcc acaccagaac gtccacgtct gcgtttggtg | 1500 |
| gatgccgatg atccactgct gcgtactgct ccaggaccag gcgaagtgtg ggttacccca | 1560 |
| gtgattggaa gccaggctcg caagtgcggc ctgcatattc gtgccggacc atacggacat | 1620 |
| gccaccgtgg aaatgcccga gtggattcac gcccacacca ccagcgatcc atggcaccca | 1680 |
| ccaggaccac tgggcctgaa gtttaagaca gtgcgcccag tggccttgcc acgagctttg | 1740 |
| gctccaccac gtaatgtgcg agtgaccggc tgctaccagt gcggaacacc agctctggtg | 1800 |
| gaaggattgg ctcccggcgg aggcaattgt cacctgacag tgaatggcga ggatgtgggc | 1860 |
| gctttcccac cgggcaaatt tgtgacagcc gccttgctga ataccccgcc accttaccaa | 1920 |
| gtgtcgtgcg gcggagaaag tgatcgtgct agcgcccgtg tgatcgatcc agctgctcag | 1980 |
| agttttaccg cgctggtgta cggcacccat accacagccg ttagtgaaac ccgtcagacc | 2040 |
| tgggccgaat gggctgctgc tcat | 2064 |

<210> SEQ ID NO 4
<211> LENGTH: 706
<212> TYPE: PRT
<213> ORGANISM: Rubella virus

<400> SEQUENCE: 4

Met Lys Leu Cys Ile Leu Leu Ala Val Val Ala Phe Val Gly Leu Ser
1               5                   10                  15

-continued

```
Leu Gly Gly Leu Gln Pro Arg Ala Asp Met Ala Ala Pro Met Pro
                20                  25                  30

Pro Gln Pro Pro Arg Ala His Gly Gln His Tyr Gly His His His
            35                  40                  45

Gln Leu Pro Phe Leu Gly His Asp Gly His His Gly Thr Leu Arg
        50                  55                  60

Val Gly Gln His His Arg Asn Ala Ser Asp Val Leu Pro Gly His Trp
65                  70                  75                  80

Leu Gln Gly Gly Trp Gly Cys Tyr Asn Leu Ser Asp Trp His Gln Gly
                85                  90                  95

Thr His Val Cys His Thr Lys His Met Asp Phe Trp Cys Val Glu His
            100                 105                 110

Asp Arg Pro Pro Pro Ala Thr Pro Thr Ser Leu Thr Thr Ala Ala Asn
        115                 120                 125

Ser Thr Thr Ala Ala Thr Pro Ala Thr Ala Pro Pro Cys His Ala
        130                 135                 140

Gly Leu Asn Asp Ser Cys Gly Gly Phe Leu Ser Gly Cys Gly Pro Met
145                 150                 155                 160

Arg Leu Arg His Gly Ala Asp Thr Arg Cys Gly Arg Leu Ile Cys Gly
                165                 170                 175

Leu Ser Thr Thr Ala Gln Tyr Pro Pro Thr Arg Phe Gly Cys Ala Met
            180                 185                 190

Arg Trp Gly Leu Pro Pro Trp Glu Leu Val Val Leu Thr Ala Arg Pro
        195                 200                 205

Glu Asp Gly Trp Thr Cys Arg Gly Val Pro Ala His Pro Gly Thr Arg
        210                 215                 220

Cys Pro Glu Leu Val Ser Pro Met Gly Arg Ala Thr Cys Ser Pro Ala
225                 230                 235                 240

Ser Ala Leu Trp Leu Ala Thr Ala Asn Ala Leu Ser Gly Gly Ser Gly
                245                 250                 255

Gly Ser Gly Gly Glu Glu Ala Phe Thr Tyr Leu Cys Thr Ala Pro Gly
            260                 265                 270

Cys Ala Thr Gln Thr Pro Val Pro Val Arg Leu Ala Gly Val Arg Phe
        275                 280                 285

Glu Ser Lys Ile Val Asp Gly Gly Cys Phe Ala Pro Trp Asp Leu Glu
        290                 295                 300

Ala Thr Gly Ala Cys Ile Cys Glu Ile Pro Thr Asp Val Ser Cys Glu
305                 310                 315                 320

Gly Leu Gly Ala Trp Val Pro Thr Ala Pro Cys Ala Arg Ile Trp Asn
                325                 330                 335

Gly Thr Gln Arg Ala Cys Thr Phe Trp Ala Val Asn Ala Tyr Ser Ser
            340                 345                 350

Gly Gly Tyr Ala Gln Leu Ala Ser Tyr Phe Asn Pro Gly Gly Ser Tyr
        355                 360                 365

Tyr Lys Gln Tyr His Pro Thr Ala Cys Glu Val Glu Pro Ala Phe Gly
    370                 375                 380

His Ser Asp Ala Ala Cys Trp Gly Phe Pro Thr Asp Thr Val Met Ser
385                 390                 395                 400

Val Phe Ala Leu Ala Ser Tyr Val Gln His Pro His Lys Thr Val Arg
                405                 410                 415

Val Lys Phe His Thr Glu Thr Arg Thr Val Trp Gln Leu Ser Val Ala
            420                 425                 430

Gly Val Ser Cys Asn Val Thr Thr Glu His Pro Phe Cys Asn Thr Pro
```

```
                   435                 440                 445
His Gly Gln Leu Glu Val Gln Val Pro Pro Asp Pro Gly Asp Leu Val
    450                 455                 460

Glu Tyr Ile Met Asn Tyr Thr Gly Asn Gln Gln Ser Arg Trp Gly Leu
465                 470                 475                 480

Gly Ser Pro Asn Cys His Gly Pro Asp Trp Ala Ser Pro Val Cys Gln
                485                 490                 495

Arg His Ser Pro Asp Cys Ser Arg Leu Val Gly Ala Thr Pro Glu Arg
                500                 505                 510

Pro Arg Leu Arg Leu Val Asp Ala Asp Asp Pro Leu Leu Arg Thr Ala
            515                 520                 525

Pro Gly Pro Gly Glu Val Trp Val Thr Pro Val Ile Gly Ser Gln Ala
        530                 535                 540

Arg Lys Cys Gly Leu His Ile Arg Ala Gly Pro Tyr Gly His Ala Thr
545                 550                 555                 560

Val Glu Met Pro Glu Trp Ile His Ala His Thr Thr Ser Asp Pro Trp
                565                 570                 575

His Pro Pro Gly Pro Leu Gly Leu Lys Phe Lys Thr Val Arg Pro Val
                580                 585                 590

Ala Leu Pro Arg Ala Leu Ala Pro Pro Arg Asn Val Arg Val Thr Gly
            595                 600                 605

Cys Tyr Gln Cys Gly Thr Pro Ala Leu Val Glu Gly Leu Ala Pro Gly
        610                 615                 620

Gly Gly Asn Cys His Leu Thr Val Asn Gly Glu Asp Val Gly Ala Phe
625                 630                 635                 640

Pro Pro Gly Lys Phe Val Thr Ala Ala Leu Leu Asn Thr Pro Pro Pro
                645                 650                 655

Tyr Gln Val Ser Cys Gly Gly Glu Ser Asp Arg Ala Ser Ala Arg Val
                660                 665                 670

Ile Asp Pro Ala Ala Gln Ser Phe Thr Gly Val Val Tyr Gly Thr His
            675                 680                 685

Thr Thr Ala Val Ser Glu Thr Arg Gln Thr Trp Ala Glu Trp Ala Ala
        690                 695                 700

Ala His
705

<210> SEQ ID NO 5
<211> LENGTH: 1338
<212> TYPE: DNA
<213> ORGANISM: Rubella virus

<400> SEQUENCE: 5
gaagaggcct ttacctactt gtgcacagcc ccaggatgcg ccacacagac acctgtgcca    60
gttcgtctgg ctggcgtgcg cttcgagagc aagattgtgg atggcggatg cttcgccccg   120
tgggatctcg aagctactgg tgcctgcatc tgcgagatcc ccacagatgt gtcctgcgaa   180
ggactcggag cttgggtgcc aacagctcca tgcgctcgca tttggaatgg aacccagcgc   240
gcctgcacat tctgggccgt gaatgcttat agcagcggcg gctatgccca gctggcctcc   300
tactttaatc aggcggcag ctactacaag cagtaccatc caaccgcctg cgaggtggaa   360
ccagccttcg acatagtga tgccgcctgc tggggattcc caaccgatac agtgatgagc   420
gtgttcgccc tggccagcta cgtgcagcat ccacataaga ccgtgcgcgt gaagttccac   480
accgagacac gtacagtgtg gcagttgagt gtggccggcg tgtcctgcaa tgtgaccacc   540
```

```
gaacatccgt tctgcaacac cccacacggc cagttggaag tgcaagtgcc accagatcca    600
ggcgatctgg tcgagtacat catgaactac accggcaacc agcagagccg ctggggactg    660
ggaagcccaa attgccatgg accggattgg gcaagcccag tgtgccaacg tcatagccca    720
gattgcagtc gcctcgtggg agccacacca gaacgtccac gtctgcgttt ggtggatgcc    780
gatgatccac tgctgcgtac tgctccagga ccaggcgaag tgtgggttac cccagtgatt    840
ggaagccagg ctcgcaagtg cggcctgcat attcgtgccg gaccatacgg acatgccacc    900
gtggaaatgc ccgagtggat tcacgcccac accaccagcg atccatggca cccaccagga    960
ccactgggcc tgaagtttaa gacagtgcgc ccagtggcct tgccacgagc tttggctcca   1020
ccacgtaatg tgcgagtgac cggctgctac cagtgcggaa caccagctct ggtggaagga   1080
ttggctcccg gcggaggcaa ttgtcacctg acagtgaatg gcgaggatgt gggcgctttc   1140
ccaccgggca aatttgtgac agccgccttg ctgaataccc cgccacctta ccaagtgtcg   1200
tgcggcggag aaagtgatcg tgctagcgcc cgtgtgatcg atccagctgc tcagagtttt   1260
accggcgtgg tgtacggcac ccataccaca gccgttagtg aaacccgtca gacctgggcc   1320
gaatgggctg ctgctcat                                                 1338

<210> SEQ ID NO 6
<211> LENGTH: 446
<212> TYPE: PRT
<213> ORGANISM: Rubella virus

<400> SEQUENCE: 6

Glu Glu Ala Phe Thr Tyr Leu Cys Thr Ala Pro Gly Cys Ala Thr Gln
1               5                   10                  15

Thr Pro Val Pro Val Arg Leu Ala Gly Val Arg Phe Glu Ser Lys Ile
            20                  25                  30

Val Asp Gly Gly Cys Phe Ala Pro Trp Asp Leu Glu Ala Thr Gly Ala
        35                  40                  45

Cys Ile Cys Glu Ile Pro Thr Asp Val Ser Cys Glu Gly Leu Gly Ala
    50                  55                  60

Trp Val Pro Thr Ala Pro Cys Ala Arg Ile Trp Asn Gly Thr Gln Arg
65                  70                  75                  80

Ala Cys Thr Phe Trp Ala Val Asn Ala Tyr Ser Ser Gly Gly Tyr Ala
                85                  90                  95

Gln Leu Ala Ser Tyr Phe Asn Pro Gly Gly Ser Tyr Tyr Lys Gln Tyr
            100                 105                 110

His Pro Thr Ala Cys Glu Val Glu Pro Ala Phe Gly His Ser Asp Ala
        115                 120                 125

Ala Cys Trp Gly Phe Pro Thr Asp Thr Val Met Ser Val Phe Ala Leu
    130                 135                 140

Ala Ser Tyr Val Gln His Pro His Lys Thr Val Arg Val Lys Phe His
145                 150                 155                 160

Thr Glu Thr Arg Thr Val Trp Gln Leu Ser Val Ala Gly Val Ser Cys
                165                 170                 175

Asn Val Thr Thr Glu His Pro Phe Cys Asn Thr Pro His Gly Gln Leu
            180                 185                 190

Glu Val Gln Val Pro Pro Asp Pro Gly Asp Leu Val Glu Tyr Ile Met
        195                 200                 205

Asn Tyr Thr Gly Asn Gln Gln Ser Arg Trp Gly Leu Gly Ser Pro Asn
    210                 215                 220

Cys His Gly Pro Asp Trp Ala Ser Pro Val Cys Gln Arg His Ser Pro
```

```
                225                 230                 235                 240
Asp Cys Ser Arg Leu Val Gly Ala Thr Pro Glu Arg Pro Arg Leu Arg
                    245                 250                 255
Leu Val Asp Ala Asp Pro Leu Leu Arg Thr Ala Pro Gly Pro Gly
                260                 265                 270
Glu Val Trp Val Thr Pro Val Ile Gly Ser Gln Ala Arg Lys Cys Gly
                275                 280                 285
Leu His Ile Arg Ala Gly Pro Tyr Gly His Ala Thr Val Glu Met Pro
                290                 295                 300
Glu Trp Ile His Ala His Thr Thr Ser Asp Pro Trp His Pro Pro Gly
305                 310                 315                 320
Pro Leu Gly Leu Lys Phe Lys Thr Val Arg Pro Val Ala Leu Pro Arg
                    325                 330                 335
Ala Leu Ala Pro Pro Arg Asn Val Arg Val Thr Gly Cys Tyr Gln Cys
                340                 345                 350
Gly Thr Pro Ala Leu Val Glu Gly Leu Ala Pro Gly Gly Gly Asn Cys
                355                 360                 365
His Leu Thr Val Asn Gly Glu Asp Val Gly Ala Phe Pro Pro Gly Lys
    370                 375                 380
Phe Val Thr Ala Ala Leu Leu Asn Thr Pro Pro Pro Tyr Gln Val Ser
385                 390                 395                 400
Cys Gly Gly Glu Ser Asp Arg Ala Ser Ala Arg Val Ile Asp Pro Ala
                    405                 410                 415
Ala Gln Ser Phe Thr Gly Val Val Tyr Gly Thr His Thr Thr Ala Val
                420                 425                 430
Ser Glu Thr Arg Gln Thr Trp Ala Glu Trp Ala Ala Ala His
            435                 440                 445

<210> SEQ ID NO 7
<211> LENGTH: 702
<212> TYPE: DNA
<213> ORGANISM: Rubella virus

<400> SEQUENCE: 7
ggactgcagc cacgcgctga tatggctgct ccaccaatgc caccacagcc accacgtgct      60
cacggacagc actacggaca ccaccatcac cagctgccat ttctgggcca cgatggacat     120
catggcggaa cactgcgtgt gggacagcat caccgtaacg ccagtgatgt gctgccaggc     180
cattggttgc aaggcggatg gggctgctac aacctgagcg attggcacca gggaacccac     240
gtgtgccaca ccaagcacat ggattttttgg tgcgtggaac acgatcgccc gccaccagct     300
acaccaacca gtctgacaac agccgccaat agcaccactg ccgctacacc agcaacagcc     360
ccaccaccat gtcacgccgg actgaatgat agctgcggcg gatttctgag cggctgcgga     420
ccaatgcgtc tgcgccatgg tgctgataca cgttgcggac gcctgatttg cggcctgagt     480
accaccgctc agtaccccac caacacgcttc ggatgcgcta tgcgttgggg actgccacca     540
tgggaactcg tggtgttgac agcccgtcca gaggatggat ggacatgtcg cggagtgcca     600
gctcatccag gcacacgttg tccagaactg gtgtccccaa tgggacgtgc cacatgtagt     660
ccagccagtg ccttgtggct ggccacagcc aatgctttga gt                       702

<210> SEQ ID NO 8
<211> LENGTH: 234
<212> TYPE: PRT
<213> ORGANISM: Rubella virus
```

```
<400> SEQUENCE: 8

Gly Leu Gln Pro Arg Ala Asp Met Ala Ala Pro Pro Met Pro Pro Gln
1               5                   10                  15

Pro Pro Arg Ala His Gly Gln His Tyr Gly His His His His Gln Leu
            20                  25                  30

Pro Phe Leu Gly His Asp Gly His His Gly Gly Thr Leu Arg Val Gly
            35                  40                  45

Gln His His Arg Asn Ala Ser Asp Val Leu Pro Gly His Trp Leu Gln
            50                  55                  60

Gly Gly Trp Gly Cys Tyr Asn Leu Ser Asp Trp His Gln Gly Thr His
65                  70                  75                  80

Val Cys His Thr Lys His Met Asp Phe Trp Cys Val Glu His Asp Arg
                85                  90                  95

Pro Pro Pro Ala Thr Pro Thr Ser Leu Thr Thr Ala Ala Asn Ser Thr
                100                 105                 110

Thr Ala Ala Thr Pro Ala Thr Ala Pro Pro Pro Cys His Ala Gly Leu
            115                 120                 125

Asn Asp Ser Cys Gly Gly Phe Leu Ser Gly Cys Gly Pro Met Arg Leu
            130                 135                 140

Arg His Gly Ala Asp Thr Arg Cys Gly Arg Leu Ile Cys Gly Leu Ser
145                 150                 155                 160

Thr Thr Ala Gln Tyr Pro Pro Thr Arg Phe Gly Cys Ala Met Arg Trp
                165                 170                 175

Gly Leu Pro Pro Trp Glu Leu Val Val Leu Thr Ala Arg Pro Glu Asp
            180                 185                 190

Gly Trp Thr Cys Arg Gly Val Pro Ala His Pro Gly Thr Arg Cys Pro
            195                 200                 205

Glu Leu Val Ser Pro Met Gly Arg Ala Thr Cys Ser Pro Ala Ser Ala
            210                 215                 220

Leu Trp Leu Ala Thr Ala Asn Ala Leu Ser
225                 230
```